United States Patent [19]

Powers, Jr. et al.

[11] 4,109,511
[45] Aug. 29, 1978

[54] METHOD AND APPARATUS FOR STATISTICALLY TESTING FRANGIBLE CONTAINERS

[75] Inventors: Whitney S. Powers, Jr., Pine City; Ross L. Hobler, Elmira; Nelson H. Bryant, Ithaca, all of N.Y.; Wilbur J. Allen, Millerton, Pa.

[73] Assignee: Powers Manufacturing, Inc., Elmira, N.Y.

[21] Appl. No.: 751,786

[22] Filed: Dec. 16, 1976

Related U.S. Application Data

[63] Continuation-in-part of Ser. No. 712,991, Aug. 8, 1976, Pat. No. 4,081,991.

[51] Int. Cl.² .......................... B07C 5/34; G01M 3/36
[52] U.S. Cl. ............................ 73/37.6; 73/45.1; 209/82
[58] Field of Search .................. 73/37, 49.2, 45.4, 53, 73/45.1, 37.6; 209/71, 111.7, 72–75, 82; 235/61.11 E, 153 AC; 346/35; 360/1; 250/223 B

[56] References Cited

U.S. PATENT DOCUMENTS

| | | | |
|---|---|---|---|
| 3,182,797 | 5/1965 | Palmer | 209/74 R |
| 3,249,224 | 5/1966 | Uhlig | 209/111.7 |
| 3,301,396 | 1/1967 | Benson et al. | 209/72 |
| 3,320,618 | 5/1967 | Kuch et al. | 346/35 X |
| 3,378,138 | 4/1968 | Brown | 209/72 |
| 3,409,129 | 11/1968 | Sperry | 360/1 X |
| 3,557,950 | 1/1971 | Powers | 209/111.7 |
| 3,581,888 | 6/1971 | Kelly | 209/74 |
| 3,745,314 | 7/1973 | Mathias et al. | 250/223 B |
| 3,751,972 | 8/1973 | Haas | 73/45.4 |
| 3,771,649 | 11/1973 | Strauss | 209/75 |
| 3,805,593 | 4/1974 | Sandoz et al. | 73/49.2 |
| 3,991,883 | 11/1976 | Hobler et al. | 209/73 |
| 4,047,000 | 9/1977 | Bryant et al. | 250/223 B X |

Primary Examiner—Daniel M. Yasich
Attorney, Agent, or Firm—Seidel, Gonda & Goldhammer

[57] ABSTRACT

Method and apparatus for statistically testing frangible containers produced by plural mold sources by selectively diverting containers to a test station at regular intervals of time. A diverted container is automatically tracked to the test station wherein it is tested. A signal indicative of the result of the test is generated for use in selectively diverting additional containers produced by the same mold source that produced the tested container. The totality of containers produced by the plural mold sources is upgraded by automatically ejecting all containers produced by one or more mold sources for fixed periods of time as a function of the test results.

19 Claims, 16 Drawing Figures

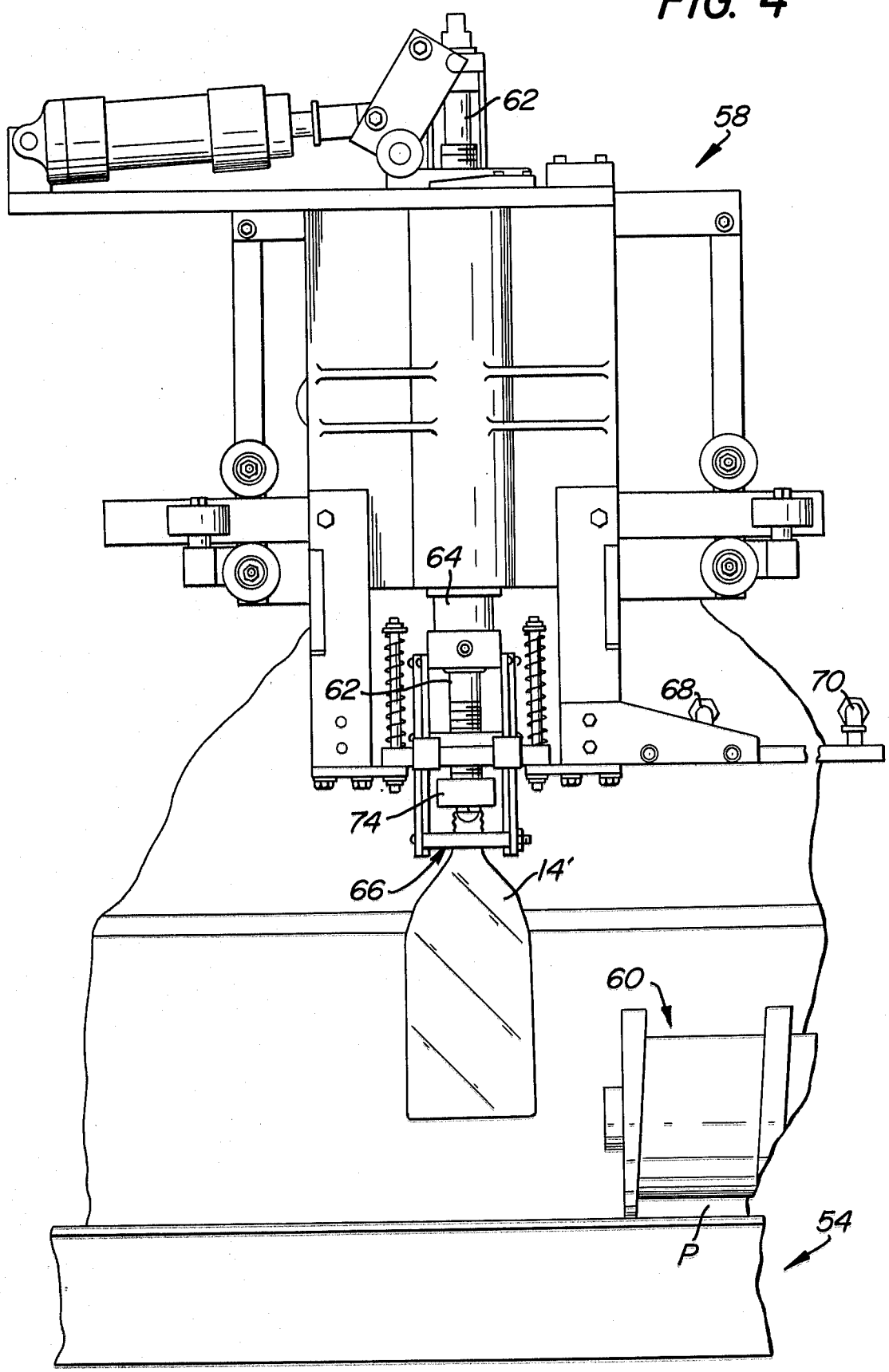

TEST CONDITION TABLE

MOLD NUMBER TABLE　　PRESSURE TESTER CYCLES TABLE

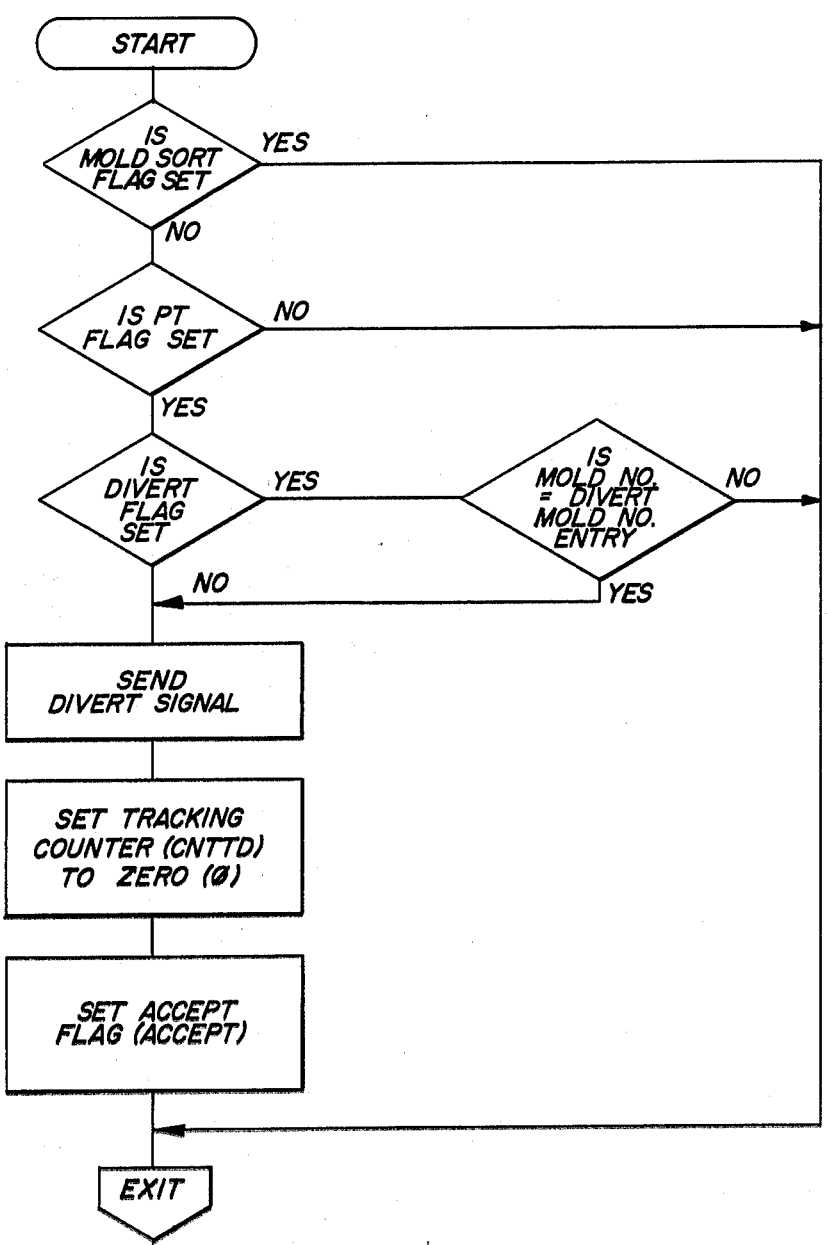

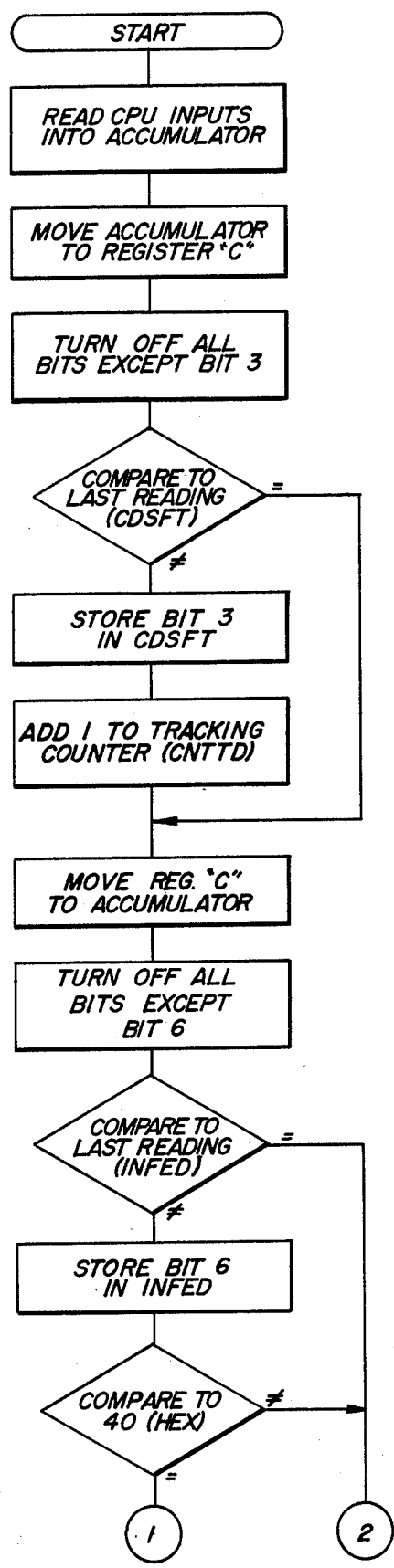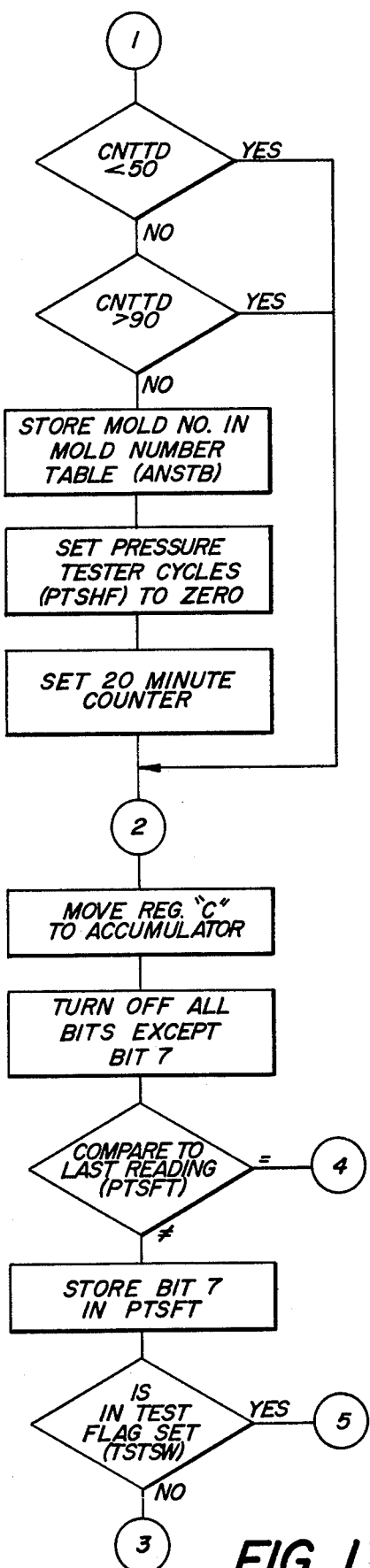
FIG. 12                                       FIG. 13

METHOD AND APPARATUS FOR STATISTICALLY TESTING FRANGIBLE CONTAINERS

RELATED APPLICATION

This is a continuation-in-part of application Ser. No. 712,991, now U.S. Pat. No. 4,081,991, for "Apparatus for Pressure Testing Frangible Containers" assigned to the assignee herein.

BACKGROUND OF THE INVENTION

The present invention is directed to testing frangible containers. In particular, the invention is directed to statistically testing the containers produced by plural mold sources in a closed-loop system and upgrading the totality of containers produced as a function thereof.

A number of hydrostatic pressure testing devices have been proposed heretofore. For example, see U.S. Pat. Nos. 2,314,310 and 3,387,704. These devices suffer from a variety of defects, making them unsuitable for application in pressure testing containers at increased rates presently demanded in the industry. These devices have not heretofore been employed in a closed-loop system for statistically testing containers.

The present invention is a pioneering design of a closed-loop system for statistically testing frangible containers. In a preferred embodiment, the system employs an advanced apparatus for performing a pressure test. Apparatus for performing other tests may however be used within the closed-loop system in addition to or in replacement of the pressure test apparatus. The particular apparatus used to perform the pressure test is described in U.S. patent application Ser. No. 712,991 invented by Whitney S. Powers, Jr. and assigned to the assignee herein. The application is incorporated herein by reference for purposes of describing specific features of the present invention.

The present invention also comprises an advanced apparatus for rapidly identifying the mold source of a container. Identification of each container by mold source is necessary to determine whether the container should be diverted to the pressure testing apparatus. The container identification apparatus is described in U.S. application Ser. Nos. 596,697 (now U.S. Pat. No. 3,991,883) and 636,875 (now U.S. Pat. No. 4,047,000), both assigned to the assignee herein. Both applications are incorporated herein by reference for the purpose of describing specific features of the invention.

The container identification and testing loop of the present invention is closed by a supervisory device such as a microcomputer. The container identification apparatus and the pressure test apparatus are interconnected to the microcomputer to enable synchronous automatic operation in transporting, diverting, statistically testing and ejecting selected containers in a procession of containers. Heretofore, it was customary to pressure test every container in such a procession. Thus, prior art techniques were time-consuming and relatively costly. Additionally, due to the inability to pressure test bottles at significantly increased rates, the prior art systems limited the number of bottles that could ultimately be packaged and shipped on a daily basis.

Prior art pressure test systems were also incapable of seizing advantage of statistical quality control techniques. The prior art systems were unable to selectively examine containers at more than one inspection rate.

Moreover, in prior art systems, a defective container was first identified and then all containers produced by the mold source that produced the defective container had to be manually discarded to upgrade the final product to be shipped.

A primary advantage of the present invention is that it automatically upgrades the final product to be shipped as a function of the pressure test results.

Another advantage of the invention is that it provides for automatic inspection of containers produced by plural mold sources with the benefit of statistical quality control techniques.

A further advantage of the invention is that it provides for the rapid and efficient testing of containers at significantly increased rates demanded by the industry.

Another advantage of the invention is that it utilizes state of the art container identification and pressure testing apparatus.

Yet another advantage of the invention is that it requires no operator intervention, statistical testing and selective ejection of the containers taking place automatically once the system loop is closed.

Other advantages will appear hereinafter in the following disclosure.

SUMMARY OF THE INVENTION

Method of statistically testing frangible containers provided with identifying indicia in respect to one or more mold sources. Each container is identified according to the indicia provided thereon. Containers are selectively diverted at regular intervals to a test station and automatically tracked after identification through the test station. The test station provides a signal indicative of the result of the test. A printed log of the test results correlated with the container identifications is automatically prepared.

If a container proves defective under test, additional containers produced by the same mold source that produced the defective container are consecutively diverted to the test station. Inspection of the additional containers under the foregoing condition is equivalent to statistically increasing the rate of inspection of containers produced by the mold source that produced the defective container.

If a defective container is detected at the increased inspection rate, all containers produced by the mold source that produced the defective container are automatically ejected for a fixed period of time to upgrade the final product to be shipped.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 4 is a front view of a pressure testing apparatus.

FIG. 5 is an electrical schematic of the container identifying apparatus data station.

FIG. 8 is a diagram of the input data format for the accumulator register.

FIGS. 11–16 are diagrams of a flow chart for operating the computer.

DETAILED DISCLOSURE OF THE INVENTION

Figure 1:
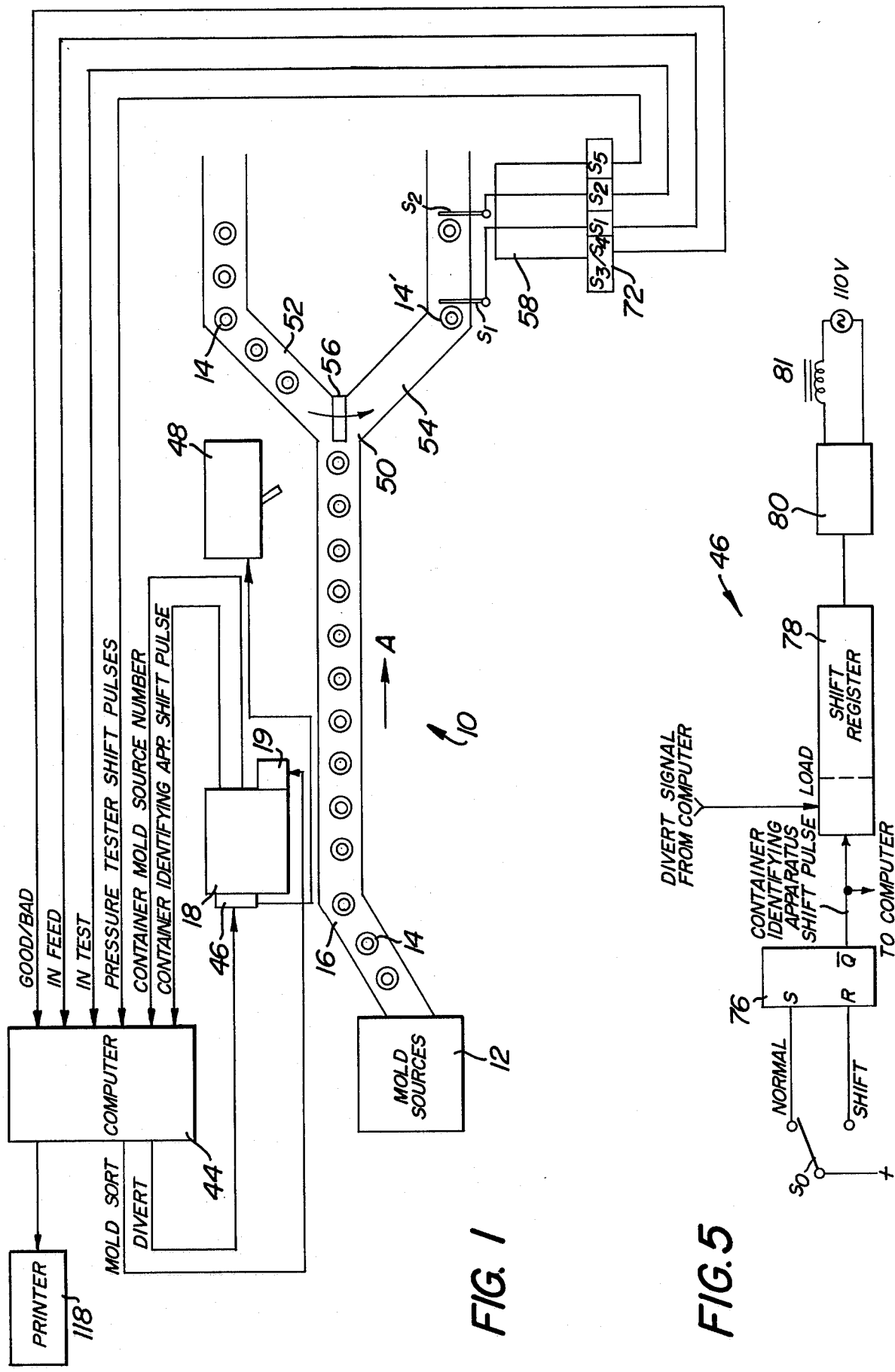
FIG. 1 is a block diagram of a closed loop system for statistically testing frangible containers according to the present invention.

Referring to the drawings in detail, wherein like numerals indicate like elements, there is shown in FIG. 1 a closed-loop system for statistically testing frangible containers according to the present invention designated generally as 10. Plural mold sources 12 produce a procession of frangible containers 14. The containers are transported on a conveyor mechanism 16 to a container identifying apparatus 18. Flow of the procession of containers on conveyor mechanism 16 is indicated by arrow A.

The container identifying apparatus 18 is described in detail in U.S. patent application Ser. Nos. 596,697 (now U.S. Pat. No. 3,991,883) invented by Hobler et al. and 636,875 now U.S. Pat. No. 4,047,000 invented by Bryant et al. Both applications are assigned to the assignee herein and are incorporated herein by reference.

Figure 2:
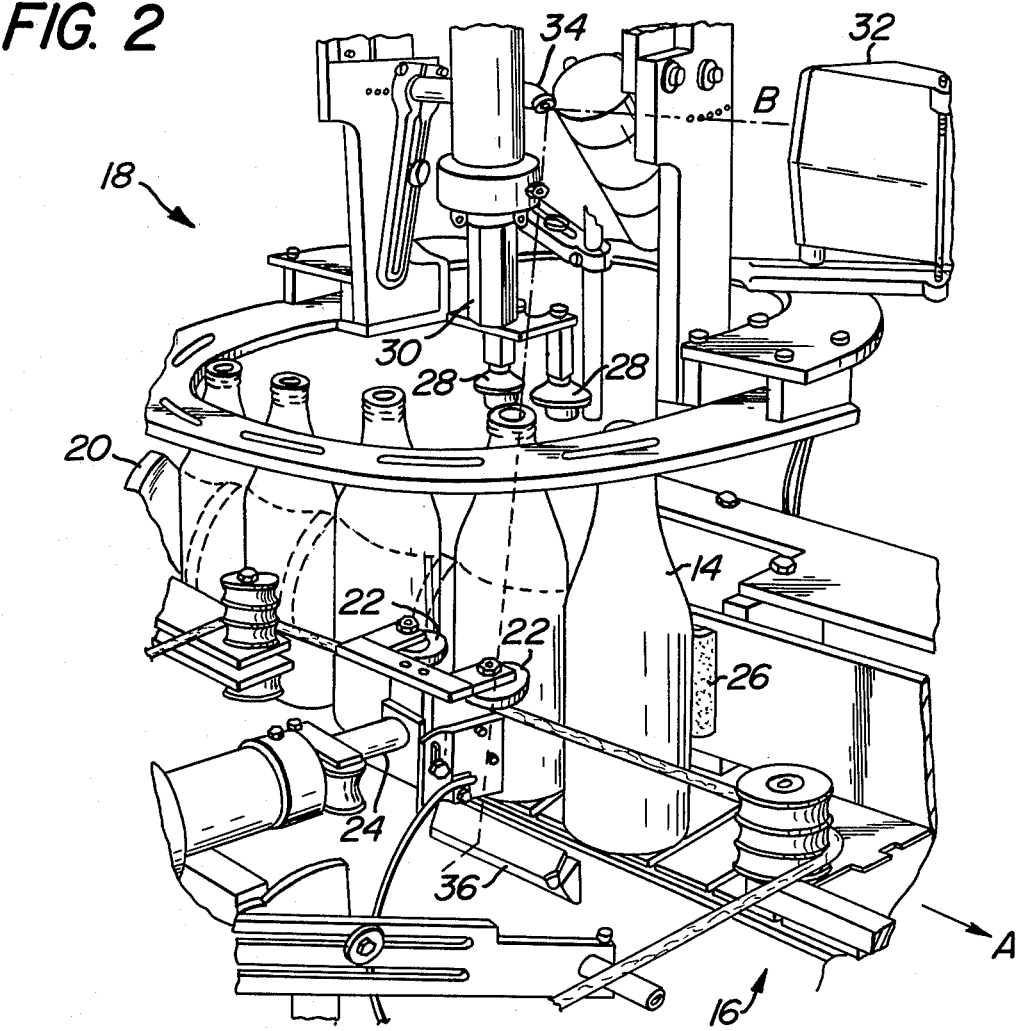
FIG. 2 is a perspective view of a container identifying apparatus.

The container identifying apparatus is shown in greater detail in FIG. 2. The procession of frangible containers 14 is transported by conveyor mechanism 16 through an inspection area. The containers are uniformly spaced apart by a screw conveyor 20. As a container enters the inspection area, it is engaged by a pair of spaced rollers 22 mounted on a plunger 24. Plunger 24 is mounted for reciprocating movement to and from the conveyor mechanism 16. The rollers 22 press the container against a belt 26 which moves in the same direction as conveyor mechanism 16. Thus, container 14 is caused to rotate about its longitudinal axis as it traverses the inspection area.

A pair of spaced neck rollers 28 hold container 14 downwardly against any vertical forces generated by rotation of the container. The neck rollers 28 are mounted on a vertically reciprocating plunger 30. The movements of plungers 24 and 30 are synchronized as described in U.S. patent application Ser. Nos. 596,697 (now U.S. Pat. No. 3,991,883) and 636,875.

A laser 32 disposed above the procession of containers 14 generates a collimated beam B. The beam B is deflected by a mirror 34 through the bottom of container 14 as the container rotates. The bottom of container 14 is provided with plural prism-like projections for dispersing the laser beam as described more fully hereinafter. As the beam emerges from the bottom of the bottle, it is deflected by a mirror 36 mounted on a stationary support along the conveyor mechanism 16. The mirror 36 intercepts the laser beam over the length of the inspection area and directs the beam to a sensor.

Figure 3:
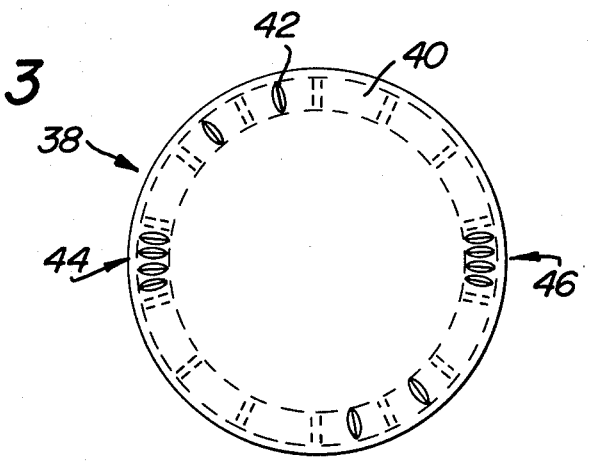
FIG. 3 is a bottom view of a frangible container.

The sensor detects dispersion of the beam caused by the prism-like projections on the container bottom. An example of a pattern of distributing the plural prism-like marks on the bottom of container 14 is shown in FIG. 3. The bottom of the container is designated 38. The peripheral zone of the container bottom 38 is segregated into plural annular sectors 40. Each annular sector 40 may be left blank or may be provided with a prism-like projection 42. The projections 42 are distributed among the annular sectors 40 to provide an optical signal representative of a binary number. Two annular sectors are provided with a plurality of contiguous projections 44 and 46 to initiate and terminate, respectively, the identification process.

The absence of a prism-like projection in an annular sector connotes a binary "0" and the presence of a projection in an annular sector connotes a binary "1". By varying the distribution of prism-like projections among the annular sectors 40, a multiplicity of binary numbers may be defined. Each binary number may serve to indicate a particular mold source which produced the container. In a preferred embodiment of the invention, the distribution of projections 42 among the annular sectors 40 above an imaginary line connecting sectors 44 and 46 is a reverse image of the distribution of projections among the annular sectors below the imaginary line. This permits two identifications to be made per full revolution of the container. Using such a scheme, six annular sectors 40 may be located above the imaginary line connecting sectors 44 and 46, and six sectors 40 may be located below the imaginary line. Discarding the case of all sectors being blank, it is possible to provide sixty-three different arrangements of the projections 42 among each set of six annular sectors. Thus, any container can be identified in connection with any one of sixty-three different mold sources.

A significant advantage of this method of container identification is that, by varying the distribution as well as the number of projections 42, a container can be identified in connection with a larger number of mold sources. Accordingly, a single container identifying apparatus 18 serves to process a large number of containers. Another advantage is that the identification process is rapid and efficient. Thus, the containers can be rotated for optical inspection while they are being transported by the conveyor mechanism 16. The containers need not be stopped during the identification process. Further description of the container identifying apparatus 18 and the advantages thereof are provided in U.S. patent application Ser. Nos. 586,697 and 636,875.

A digital signal representative of the container mold source number is generated by the container identifying apparatus 18. See FIG. 1. The digital signal is supplied to a computer 44 which supervises the statistical testing described hereinafter. The computer 44 generates a "divert" signal which is supplied to a data station 46 operatively associated with the container identifying apparatus 18. The data station 46 controls the operation of an air pump 84 located adjacent a conveyor junction 50. At junction 50, conveyor mechanism 16 branches into conveyor mechanism 52 and 54 which may be separated by a swingable gate 56. Containers which are not to be tested are transported by conveyor mechanism 16 to conveyor mechanism 52 to a packaging station or the like. On the other hand, containers which are to be tested are diverted by operation of air pump 48 through gate 56 to conveyor mechanism 54. In the preferred embodiment described herein, conveyor mechanism 54 transports the diverted container to a pressure tester 58. It should be understood, however, that testing units for testing physical properties of a container such as wall thickness and dimensional gaging may also be used in the system in addition to or in replacement of pressure tester 58.

Pressure tester 58 is shown in detail in FIG. 4. The pressure tester accepts a diverted container, designated as 14', and subjects it to high hydrostatic pressures such as 200 psi. During pressure testing, the container is suspended above the conveyor mechanism 54. The diverted containers 14' are transported along the conveyor mechanism 54 at a rate synchronized with a screw conveyor 60. Screw conveyor 60 maintains successively diverted containers 14' apart by a predetermined distance.

A pressure conduit 62 is surrounded by a vertically reciprocating hollow shaft 64. Hollow shaft 64 and pressure conduit 62 are not connected together, but each are guided for vertical movement as described in U.S. patent application Ser. No. 712,991.

A pair of cooperating jaws 66 is disposed at the lower end of hollow shaft 64 for vertical reciprocating movement therewith. The jaws 66 open and close as a function of the elevation of shaft 64. The jaws 66 grasp the container 14' and lift the container off conveyor mechanism 54 during the hydrostatic pressure test.

Prior to pressure testing, while the diverted container 14 is conveyed by screw conveyor 60 along conveyor mechanism 54, the container is pre-filled with water by means of nozzles 68 and 70. By the term "pre-filled", it is meant that the container is partially filled with water such that only a small volume of the container at its neck portion is left unfilled. Nozzles 68 and 70 are spaced apart by the pitch of screw conveyor 60. Nozzle 68 is spaced apart from pressure conduit 62 by the same pitch. The nozzles are controlled by solenoid operated valves switched on and off by a data station 72 operatively associated with the pressure tester 58. See FIG. 1.

The pre-filled container 14' is grasped by jaws 66 and lifted off conveyor mechanism 54. See FIG. 4. The neck of the container is engaged by a sealing head 74 connected to pressure conduit 62. Water flows under pressure through conduit 62 to completely fill container 14' while it is suspended above conveyor mechanism 54. The container 14' is subjected to hydrostatic pressure such as 200 psi for a short period of time after which the conduit 62 and jaws 66 descend to conveyor mechanism 54. At the end of a cycle of operation of the pressure tester, container 14' is returned to the conveyor mechanism and jaws 66 open to release the container. The pressure testing operation is repeated for the next diverted container 14' conveyed by screw conveyor 60.

If a container fails during a pressure test, a pressure transducer indicates the same by generating a digital signal designated "good/bad". See FIG. 1. This signal is supplied to computer 44 for the purpose of supervising further pressure testing as well as selective ejection of containers produced by the mold source which produce the defective container. Operation of the pressure tester 58 is described in greater detail in U.S. patent application Ser. No. 712,991. Further description herein is not deemed necessary.

Tracking a Container to be Diverted

When a container 14 is identified by container identifying apparatus 18, a digital signal representative of the container mold source number is generated as disclosed in U.S. patent application Ser. Nos. 596,697 and 636,875. The digital signal representative of the container mold source number is supplied to computer 44. See FIG. 1. The computer 44 includes a read/write memory for storing information corresponding to each mold source. One of the bits of information stored for each mold source is a flag bit designated "PT flag" for indicating whether an identified container 14 should be diverted by air pump 48 to conveyor mechanism 54 for purposes of testing by pressure tester 58. As will be described more fully hereinafter, the "PT flag" bit for each mold source undergoes a regular or cyclic change of state. Preferably, each "PT flag" bit changes state every twenty minutes to indicate that a container from a particular mold source should be diverted for pressure testing.

If the "PT flag" bit for the mold source number identified by container identifying apparatus 18 indicates that the container 14 should be diverted for pressure testing purposes, the computer 44 generates a "divert" signal. The "divert" signal is supplied to data station 46 associated with container identifying apparatus 18. Thereafter, data station 46 tracks the movement of container 14 to the air pump 48.

The data station 46 comprises a cam operated switch S0 which alternates between a "normal" and a "shift" position as a function of the cyclic operation of container identifying apparatus 18. See FIG. 5. Preferably, the rate of operation of the container identifying apparatus is synchronized to the speed of conveyor mechanism 16 by driving the apparatus and conveyor mechanism through appropriate gearing off a common motor. Switch S0 is then driven by a cam mounted at the rear of the drive shaft for container identifying apparatus 18. the switch, however, may be driven by any other suitable means apparent to one of ordinary skill in the art to provide an indication of the rate of movement of a container on conveyor mechanism 16.

Switch S0 toggles a set-reset flip-flop 76. See FIG. 5. The complementary output of flip-flop 76 is used to clock a shift register 78 having a first stage which is loaded with a binary "1" by the "divert"0 signal. The first stage of the shift register is shown to the left of the vertical dotted line in FIG. 5. The complementary output of flip-flop 76 is denominated "container identifying apparatus shift pulse". This shift pulse is supplied to the computer 44 for purposes described hereinafter.

The number of stages of shift register 78 is determined by the relative speeds of container identifying apparatus 18 and conveyor mechanism 16 and the distance separating air pump 48 from the cntainer identifying apparatus. Preferably, the air pump is disposed adjacent to conveyor junction 50 downstream from container identifying apparatus 18 such that, after an integral number of cycles of operation of the container identifying apparatus, the identified container 14 has been transported by conveyor mechanism 16 to a point adjacent the nozzle of air pump 48. The number of stages of shift register 78 is preferably made equal to the number of cycles of operation of the container identifying apparatus 18 required to bring the container 14 to the air pump nozzle. Simultaneous with the movement of container 14 to a position adjacent the air pump nozzle, the contents of the first shift register stage will be shifted to the last or output stage of the shift register.

The output stage of the shift register drives a solid state relay 80 which operates a solenoid 81 to cause the air pump to produce a blast of air which diverts container 14 to conveyor mechanism 54. See FIG. 5. A gate 56 may be interposed at the conveyor junction 50 to prevent containers from being diverted accidentally to conveyor mechanism 54 when the air pump is not actuated. See FIG. 1.

It is preferred that the set-reset flip-flop 76 comprise interconnected open collector lamp drivers such as the Allen Bradley 1602 drivers. the shift register 78 may comprise three series connected four-bit shift registers such as the Allen Bradley 1720-L811 four-zone shift registers. Thus, in the preferred embodiment, shift register 78 is a twelve-bit shift register clocked every cycle of operation of container identifying apparatus 18. The twelfth bit corresponds to the container position at air pump 48.

Shift register 78 is capable of tracking more than one container at a time. Thus, at least one of a plurality of containers produced by each of the plural mold sources is identified, tracked and diverted at regular intervals of twenty minutes. Within any such twenty minute interval, plural containers, each produced by a different mold source, may be scheduled for diversion to the pressure tester. Accordingly, the first stage of shift register 78 may be loaded at the conclusion of successive cycles of operation of the container identifying apparatus by consecutive "divert" signals. At any given instant of time, then, the shift register can track plural containers scheduled for diversion and testing.

Tracking a Diverted Container

In the embodiment of the invention described herein, the great majority of containers will not be diverted to conveyor mechanism 54. Thus, the combined rate of production of containers by plural mold sources 12 exceeds the system test rate. Containers which are not diverted proceed from conveyor mechanism 16 past air pump 48 to conveyor mechanism 52 where they are transported to further testing stations, packaging stations and so forth. See fIG. 1.

Diverted containers, on the other hand, pass through gate 56 to conveyor mechanism 54 which transports the containers to presure tester 58. Between the time that the container 14' is diverted to conveyor mechanism 54 by air pump 48 and the time that the diverted container is accepted by the pressure tester 58, shift register 78 does not track the movement of the container. Shift register 78 only tracks containers between container identifying apparatus 18 and air pump 48. As will be described more fully hereinafter, the container is tracked by computer 44 between the air pump and pressure tester.

Tracking of the diverted container continues as the container enters a pocket P in screw conveyor 60 at the pressure tester station. See FIG. 4. The entry of the diverted container into a screw conveyor pocket is signaled by a trip switch S1 which causes data station 72 to generate an "in feed" signal to computer 44. See FIG. 1. The trip switch S1 includes an extended arm which juts into the path of the diverted containers 14'. Preferably, trip switch S1 is vertically disposed at an elevation along the neck portions of the containers. The trip switch is laterally disposed adjacent the upstream or entry end of the screw conveyor.

The downstream or exit end of the screw conveyor 60 is located adjacent the pressure tester 58 such that a diverted container 14' in the last pocket of the screw conveyor actuates a trip switch S2 just before the container is grasped by jaws 66 and lifted off conveyor mechanism 54 for pressure testing. See FIG. 1. Trip switch S2 is identical to trip switch S1 and is vertically disposed in the same manner as switch S1 to obstruct the passage of the neck of a container 14'. Trip switch S2 causes data station 72 to generate an "in test" signal which is supplied to the computer 44 for purposes discussed hereinafter.

Figure 6:
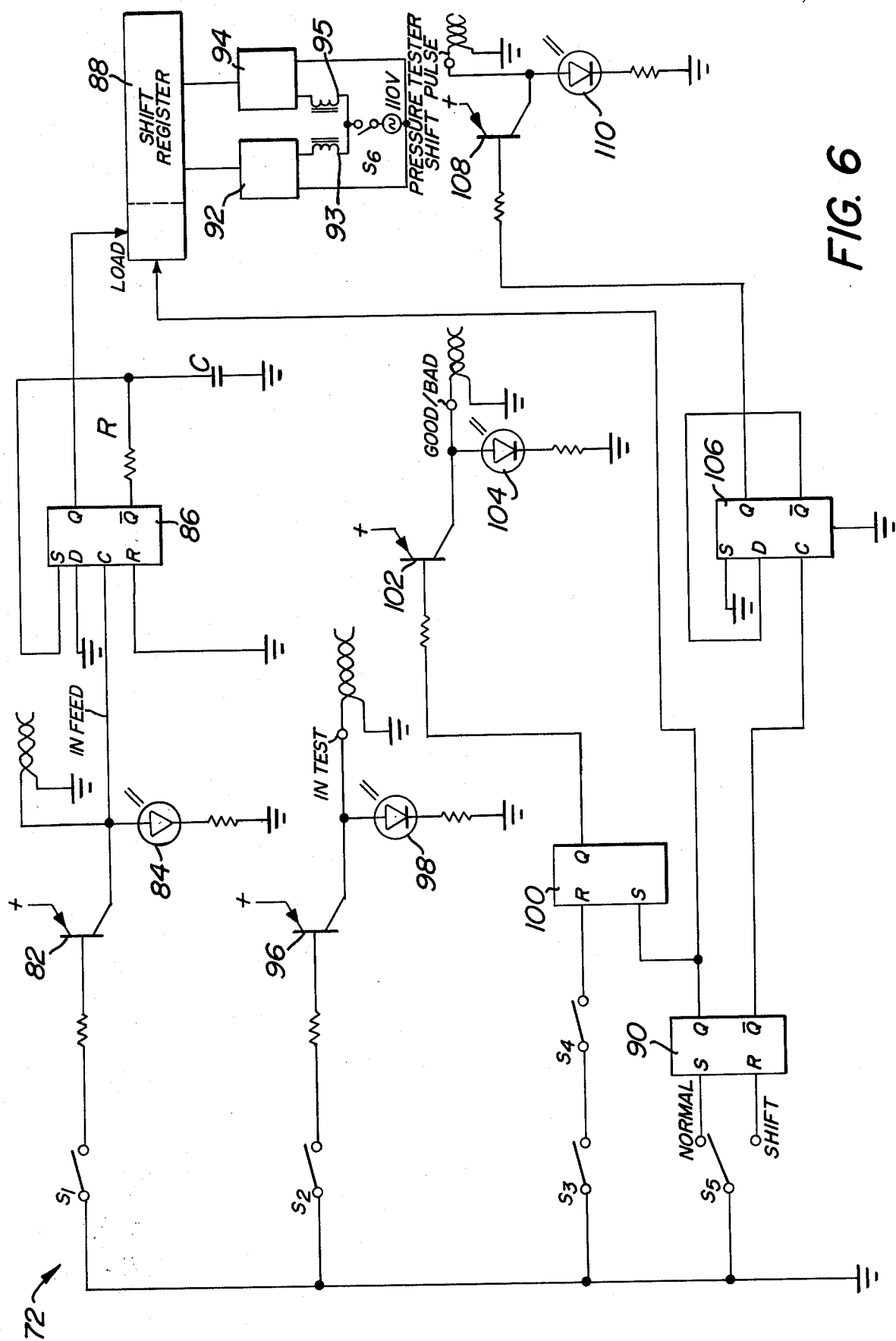
FIG. 6 is an electrical schematic of the pressure tester data station.

Data station 72 is shown in detail in FIG. 6. Trip switch S1 operates a transistor 82 provided with a light emitting diode 84 in its collector circuit. The "in feed" signal is generated at the collector terminal of the transistor and is supplied to computer 44 over twisted cable or the like. The "in feed" signal also clocks a D-type edge triggered flip-flop 86 connected to external elements R and C. Flip-flop 86 generates a brief output or "load" pulse in response to the "in feed" signal. The "load" pulse loads the first stage of a shift register 88 with a binary "1". Thus, the first stage of shift register 88 is loaded when a diverted container 14' trips switch S1 and enters the first pocket of the screw conveyor 60. The "load" pulse generated by flip-flop 86 therefore indicates that a diverted container 14' has been accepted by the pressure tester 58.

Shift register 88 operates in substantially the same manner as shift register 78 to track a diverted container 14' as it is conveyed by screw conveyor 60 at the pressure tester. Shift register 88 is clocked by a cam operated switch S5 which alternates between a "normal" and a "shift" position as a function of the cyclic operation of pressure tester 58. Preferably, the rate of operation of the pressure tester is synchronized to the speed of the screw conveyor by driving the apparatus and screw conveyor through appropriate gearing off a common motor. In the embodiment described herein, the screw conveyor advances one pocket for each cycle of operation of the pressure tester. Switch S5 is then operated by a cam mounted on the drive shaft of the pressure tester. The switch, however, may be driven by any other suitable means apparent to one of ordinary skill in the art to provide an indication of the rate of movement of a container in screw conveyor 60.

Once every cycle of operation of the pressure tester, the switch S5 is deflected to the "shift" position and returns to the "normal" position. The alternating operation of switch S5 sets and resets a set-reset flip-flop 90. Thus, each cycle of operation of pressure tester 58, a shift pulse is generated at the Q output of flip-flop 90. This shift pulse clocks shift register 88 so that the contents of the first stage of the shift register are advanced stage by stage as the container advances from pocket to pocket of the screw conveyor. The jaws of the pressure tester will always be in position to grasp a bottle in the last pocket at the downstream end of the screw conveyor 60 since the pressure tester is synchronously driven with the screw conveyor. Preferably, the movement of the container into the last pocket in the screw conveyor is indicated by one of the later stages of shift register 88.

It should be understood that in the foregoing description of operation of the pressure tester and screw conveyor, the term "pocket" is used to indicate a recessed area of the screw conveyor in which a container may be transported. Physically, of course, the screw conveyor consists of a continuous thread which gives the appearance of laterally translating pockets as the conveyor revolves about its longitudinal axis.

In the preferred embodiment, the number of stages of shift register 88 is at least equal to the number of pockets in screw conveyor 60. In other words, the number of stages of shift register 88 is at least equal to the maximum number of containers 14' that the screw conveyor can hold in a given instant of time. This, of course, is a function of the pitch of the screw conveyor. It is preferred that the screw conveyor be able to accommodate as many as five containers at a given instant of time.

Since it may be desired to indicate the progressive movement of the container after it has been removed from the screw conveyor under test, the shift register may be provided with additional stages. These stages may be used to drive display devices to indicate the lateral postion of the container during testing. Accordingly, shift register 88 may be as long as eight bits or more. For example, shift register 88 may comprise two series connected Allen Bradley 1720-L811 four-zone shift registers. Five stages of such a shift register will mark the five pockets of the screw conveyor. The remaining three stages can be used to continue to track the container 14′ after it has been removed from the screw conveyor and as it is being subjected to pressure testing.

As mentioned previously, the nozzles 68 and 70 are separated by a distance equal to the pitch of the screw conveyor. See FIG. 4. In addition, nozzle 68 is separated from the pressure conduit 62 by the same distance. Accordingly, the two continuous stages of shift register 88 immediately preceding the fifth stage may be used to operate nozzles 68 and 70 by means of solid state relays 92 and 94, respectively. See FIG. 6. Solid state relays 92 and 94 energize solenoids 93 and 95 to control nozzles 70 and 68, respectively.

The fifth stage of the shift register indicates that a container 14′ is present in the downstream end pocket of the screw conveyor 60 and is ready to be grasped by jaws 66 and pressure tested. Thus, using a five pocket screw conveyor and an eight stage shift register, the third and fourth stages of the register will respectively indicate that a diverted container 14′ moves successively into position beneath nozzles 70 and 68. Nozzles 70 and 68 can then be successively activated to progressively pre-fill the container with water in two discrete steps.

Specifically, as the containers move beneath the nozzles 70 and 68, The third and fourth stages of shift register 88 successively activate solid state relays 92 and 94. See FIG. 6. In turn, relays 92 and 94 energize solenoids 93 and 95, respectively, to consecutively operate nozzles 70 and 68. The duration that the nozzles 68 and 70 are maintained "on" by solenoids 93 and 95 is set by a switch S6 operated by a cam mounted on the drive shaft of the pressure tester 58. The cam is designed to keep the nozzles on long enough to pre-fill the container to a desired level.

Data station 72 includes a trip switch S2. The trip switch operates a transistor 96 having a light emitting diode 98 in its collector circuit. The collector terminal of the transistor supplies the "in test" signal which indicates that the diverted container 14′ is just about to be grasped by jaws 66 of pressure tester 58 and subjected to a hydrostatic test. The "in test" signal is also supplied by means of twisted cable or the like to computer 44 for purposes discussed hereinafter.

Switches S3 and S4 are series connected switches. Switch S3 is a pressure operated switch connected to the pressure conduit 62. A defective container will prevent the pressure conduit 62 from reaching a predetermined threshold pressure, preventing the pressure switch S3 from closing. Switch S4 is a cam operated switch which is temporarily closed at a predetermined point of the pressure tester cycle by a cam mounted on the drive shaft of the pressure tester.

Switches S3 and S4 are connected in series to the reset terminal of set-reset flip-flop 100. The flip-flop 100 drives a transistor 102 provided with a light emitting diode 104 in its collector circuit. The collector terminal of the transistor carries the "good/bad" signal supplied to computer 44. The set terminal of flip-flop 100 is driven by the Q output of flip-flop 90. As mentioned previously, the Q output of flip-flop 90 clocks shift register 88. Accordingly, once every cycle of operation of pressure tester 58, shift register 88 is clocked and flip-flop 100 is set. If the container 14′ under test is defective, switch S3 remains open and flip-flop 100 remains set. But if the container 14′ is good, switch S3 will close and, during the portion of operation of the pressure tester for which switch S4 closes, flip-flop 100 will reset. As a result, the "good/bad" signal generated at the collector terminal of transistor 102 changes state to indicate a defective container.

The complementary or Q output of flip-flop 90 carries the inverse of the shift signal used to clock shift register 88. The complementary output of flip-flop 90 clocks a D-type edge triggered flip-flop 106 connected to operate in a toggle mode. Thus, once each cycle of operation of pressure tester 58, the flip-flop 106 changes state. Flip-flop 106 drives a transistor 108 having a light emitting diode 100 in its collector circuit. The collector terminal of the transistor carries the "pressure tester shift pulse" signal supplied to computer 44 by twisted cable or the like.

Of course, the light emitting diodes 84, 98, 104 and 110 may be omitted from their respective collector circuits. It has been found, however, that the light emitting diodes are of assistance in providing manual supervision of the overall operation of the statistical test system.

In summary, in tracking a diverted container 14′, trip switch S1 closes when the container first enters a pocket of screw conveyor 60. Thereafter, shift register 88 tracks the movement of the container. When the container enters the last or downstream end pocket of the screw conveyor, this is indicated by the contents of one of the later stages of shift register 88. Immediately before the container is grasped by jaw 66 of pressure tester 58, trip switch S2 is operated. The lateral movement of the container may continue to be tracked by the shift register. During the pressure test itself, switch S4 is temporarily closed at a predetermined point of the pressure tester cycle to interrogate the state of pressure switch S3. If the container under test is good, switch S3 will close causing flip-flop 100 to change state. The change of state of flip-flop 100 is reflected in the "good/bad" signal.

Set-reset flip-flops 90 and 100 may comprise interconnected lamp driver inverters such as Allen Bradley lamp drivers. D-type edge triggered flip-flops 86 and 106 may be National Semiconductor 4613A/5613A flip-flops or the equivalent.

Statistical Testing

Figure 7:
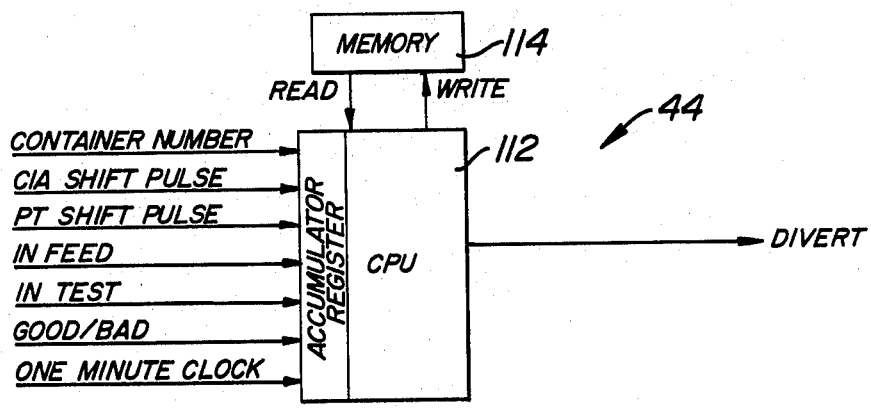
FIG. 7 is a block diagram of the computer architecture.

Statistical testing of the containers 14 by container identifying apparatus 18 and pressure tester 58 is supervised by the computer 44 in response to the output signals generated by the container identifying apparatus and the pressure tester. See FIG. 1. Preferably, computer 44 is a microcomputer using a modular central processor unit and memory and input/output units such as those manufactured by the Intel Corporation. The computer structure is schematically represented in FIG. 7. The central processor unit 112 includes an accumulator register for processing the signals appearing at the input port of the central processor unit. As shown in FIG. 7, the signals appear to the input port in a group of eight bits or a byte. The byte includes the "in feed", "in test" and "good/bad" signals and the "container identifying apparatus" and "pressure tester" shift pulses. The central processor unit periodically scans its input port according to a program stored in memory 114. The input signals provide the central processor unit with data in respect to the movement of a container, whether the container should be tested, and the results of a pressure test of the container. In response, the central processor unit generates the "divert" signal used by the container identifying apparatus data station 46 to operate the air pump 48.

The data format for a byte of information appearing at an input port of the central processor unit is shown in FIG. 8. Data bits 0-2 are signal bits not pertinent to the present invention. These bits provide information as to the general operation of the container identifying apparatus 18. Bits 3-7 are the afore-mentioned "in test", "good/bad", "in feed" and "shift pulse" signals. The input signals are periodically scanned and accumulated in the accumulator register in the format shown as will be described in greater detail hereinafter.

Figure 9:
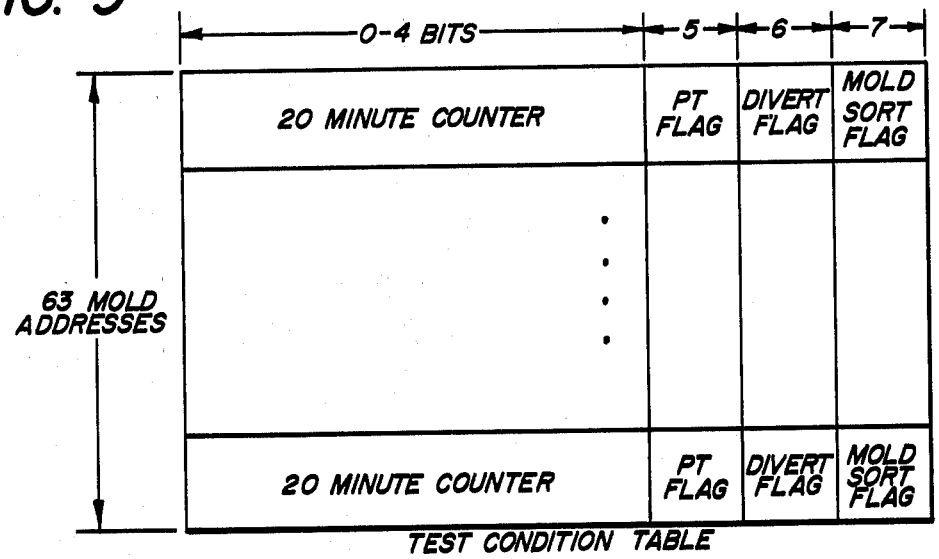
FIG. 9 is a diagram of the "test condition" table in the computer memory.

Memory 114 includes a read/write portion which contains a "test condition" table as shown in FIG. 9. The "test condition" table contains a byte of data for each of the plural mold sources 12. Preferably, the table is capable of carrying 127 bytes corresponding to 127 sources. Each address corresponds to a different mold source. Data bits 0-4 comprise a "twenty minute counter" portion of the byte. The "twenty minute counter" bits determine the initial testing rate for the containers produced by each mold source. The fifth data bit is the "PT flag" bit. The sixth data bit is the "divert flag". The seventh bit is the "mold sort flag" bit. The term flag bit is used in its conventional sense herein, namely, a memory bit used to store a bit of information.

A one minute clock 116 periodically causes the "twenty minute counter" bits to be read out of memory 114 into one of a plurality of general purpose registers internal to the central processor unit. The register is then decremented one count and its contents are written back into the "twenty minute counter" bits.

The "twenty minute counter" bits are preset to the decimal 20 when an "in test" signal is received by the central processor unit provided that the "good/bad" signal does not indicate a defective container. After twenty minutes have passed, the "twenty minute counter" bits will have been decremented to zero. At this time, the central processor unit causes the "PT flag" bit to change state to indicate that the next container identified by container identifying apparatus 18 should be subjected to a pressure test at tester 58. Thus, at least one container from each mold source will be subjected to pressure testing every twenty minutes. Of course, the initial frequency of testing can be varied by setting bits 0-4 of the "test condition" table to a number other than 20.

If the "PT flag" bit indicates that a container identified at container identifying apparatus 18 should be pressure tested, the central processor unit generates the "divert" signal. The "divert" signal loads shift register 78 in data station 46. See FIG. 5. Shift register 78 then tracks the container from container identifying apparatus 18 to air pump 48. When the container comes into position adjacent the air pump, the shift register 78 operates solid state relay 80. The solid state relay activates the air pump to divert the container to conveyor mechanism 54 and pressure tester 58.

At the time the "divert" signal is generated by the central processor unit, a "tracking counter" located within the unit is set to zero. This counter is incremented by each shift pulse generated at the complementary output of flip-flop 76 in data station 46. Each such shift pulse indicates the completion of a cycle of operation of the container identifying apparatus. The "tracking counter" tracks the movement of the container until the container is diverted and accepted by the pressure tester 58. The contents of the counter are compared to lower and upper predetermined limits which define a "time window" within which a container scheduled for pressure testing can be expected to reach switch S1 at the pressure tester. The "time window" limits are stored in a read-only portion of memory 114. The limits are based on experience and represent the minimum and maximum transport times for a container from the container identifying apparatus to the pressure tester.

Figure 10:
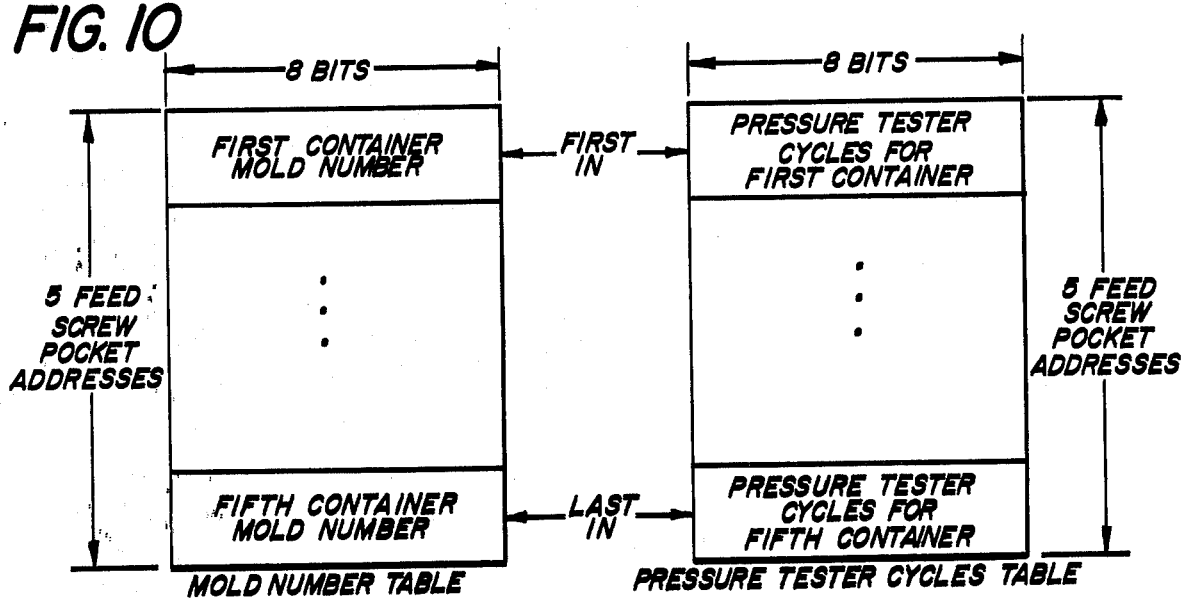
FIG. 10 is a diagram of the mold number and pressure testers tables in the computer memory.

If the contents of the counter are within the "time window", the mold number of the container is stored in a "mold number" table in the read/write portion of memory 114 when switch S1 is tripped. See FIG. 10. The mold number table is a FIFO table containing entries which represent different mold source numbers. Preferably, the number of entries which can be made in the mold number table is at least equal to the number of pockets in screw conveyor 60. At any given instant of time, then, the entries in the "mold number" table indicate the mold sources of all diverted containers in transit in the screw conveyor. The container mold numbers are stored in the mold number table in the order to which the containers reach the screw conveyor. Thus, the topmost entry is for the first container to reach the screw conveyor. The bottommost entry is for the container to last reach the screw conveyor.

The read/write portion of memory 114 also includes a "pressure tester cycles" table. See FIG. 10. This table is also a FIFO table and has the same capacity as the "mold number" table. Each entry in the "pressure tester cycles" table represents the number of pressure tester cycles which have been completed for a particular container during the time elapsed since the acceptance of the container at the screw conveyor. An entry in the "pressure tester cycles" table is set to zero when the container trips switch S1. Thereafter, the entry is incremented one count in response to each "pressure tester shift" pulse generated by data station 72.

The "mold number" and "pressure tester cycles" tables are complementary tables which together define the absolute position of a container at the screw conveyor. There is a one-to-one correspondence between the entries of the "mold number" and "pressure tester cycles" tables. Entries in both tables are made on a FIFO basis and in the same order. The "mold number" table indicates the order in which diverted containers are accepted by the screw conveyor but does not indicate the number of pockets separating containers at the screw conveyor. This information is provided by the "pressure tester cycles" table. For the embodiment described herein, the difference between the numbers of pressure tester cycles completed for any two containers indicates the number of pockets separating the containers since the screw conveyor advances exactly one pocket for each cycle of operation of the pressure tester.

The fourth and fifth cycles of operation of the pressure tester are particularly important. In the preferred embodiment, the screw conveyor is provided with five pockets. A container will advance one pocket for each cycle of operation of the pressure tester. As the pressure tester completes the fourth cycle of operation, the container is moved into the fifth or last pocket at the downstream end of the screw conveyor. At this time, the pressure tester starts its fifth cycle of operation by grasping the container at its neck portion.

Very shortly thereafter, before the container is lifted off conveyor mechanism 54 for purposes of pressure testing, the container trips switch S2. Accordingly, data station 72 generates an "in test" signal for use by computer 44. See FIG. 1. In response to the "in test" signal, the central processor unit sets "in test" and "results" flag bits in the read/write portion of memory 114 to binary "1" and "0", respectively.

Briefly following the generation of the "in test" signal, the pressure tester lifts the container off conveyor mechanism 54. The pressure tester proceeds to execute its fifth cycle of operation with respect to the container. During the fifth cycle of operation, switch S4 closes to interrogate switch S3 as to whether the container is defective. See FIG. 6. The central processor unit adjusts the "results" flag bit as a function of the "good/bad" input.

If the container is not defective, the "good/bad" signal is a binary "1". If the container is defective, the "good/bad" signal is a binary "0". If the container is not defective, the central processor unit sets the "results" flag to a binary "1". If the container is defective, the central processor unit leaves the "results" flag at a binary "0".

A. Internal Self-Test

Following the end of the fourth cycle of operation of the pressure tester, the central processor unit performs an internal test to guarantee that the results of the upcoming test will be applied to the correct container. To perform the test, the central processor unit checks the "pressure tester cycles" table. See FIG. 10. Specifically, the central processor unit reads out the first entry in the "pressure tester cycles" table and compares that entry to the number 4, the number of cycles of operation completed by the pressure tester since the acceptance of the container by the screw conveyor. If the container was properly diverted to the screw conveyor and not tampered with, the comparison will result in an equality. In that case, the central processor unit will read out the "results" flag bit from memory 114 on completion of the pressure test. Additionally, the central processor unit will read out the first entry in the "mold number" table and build a print line in memory 114 which includes the mold number of the container tested as well as the test results.

If the comparison indicates that the entry in the "pressure tester cycles" table is less than the number 4, it indicates that the container has either been manually inserted downstream of switch S1 or advanced manually one or more pockets after tripping the switch. In either case, the central processor unit will not read out the "results" flag bit. In effect, the pressure test will be completely disregarded by the computer.

If the comparison indicates that the entry in the "pressure tester cycles" table is greater than the number 4, it indicates that the container had been removed from the screw conveyor and either never replaced or replaced in an upstream pocket. Again, the central processor unit completely disregards the results of the pressure test.

At the end of the fifth cycle of operation of the pressure tester, or at any convenient time following the above comparison test, the "mold number" and "pressure tester cycles" tables are adjusted by the central processor unit. Specifically, following the comparison test, the first entry in the "mold number" table is erased and the other entries are shifted forward one location. The mold number of the next container to be accepted by the screw conveyor will then be fed into the last location in the table. As the contents of the "mold number" table are shifted forward one location, the "pressure tester cycles" table entries are incremented one count and shifted forward one location as well. In this manner, the central processor unit readies itself for the next container to be tested.

B. Increasing The Test Rate And Upgrading The Product

If a container tested at the initial test rate of one container per 20 minutes is defective, the "good/bad" signal generated by data station 72 will be a binary "0". The central processor unit will then set the "divert" flag in memory 114 and reset a "ten minute counter" in the memory to zero. Additionally, a "divert" counter in the memory is set to 4. As will be seen hereinafter, the "divert" counter could also be set to any other number which indicates the number of containers to be consecutively diverted at the increased test rate from the mold source which produced the defective container.

Thereafter, the contral processor unit determines whether the "divert" flag is set for a particular container. If so, the central processor unit checks the container mold source number against a "divert mold number" table maintained in memory. This is a single entry table which is loaded with the first entry in the "mold number" table when the "divert" flag is first set. The entry is not changed until all four containers have been tested at the increased rate. If the container mold number is identical to the "divert mold number" table entry, it indicates that the container is one of four containers being consecutively diverted for testing, each of which are produced by the same mold source.

Operation of the system in response to the "divert" flag is very similar to operation in response to the "PT flag". Each container diverted in response to the "divert" flag results in the "divert" counter being decremented one count. If the diverted container is not defective, a print line is built including the container mold number and the test results. If, on the other hand, the diverted container is defective, a "bad" flag in memory 114 is set, and a print line is built including the container mold number and test results. The purpose of the "bad" flag is explained more fully hereinafter.

Regardless of the condition of a container diverted at the increased test rate in response to the "divert" flag, following the build-up of a print line, the central processor unit checks the "divert" counter and the "ten minute counter". It is expected that more than four containers can be produced by a mold every ten minutes. Thus, the "divert" counter will normally reach zero before the "ten minutes counter". If neither are zero, the foregoing steps are repeated as consecutive testing of four containers from the same mold source has not been completed. If either are zero, it indicates that testing at the increased rate is completed. The "bad" flag is then checked. If it is set, the central processor unit sets a "mold sort" flag in the appropriate "test condition" table entry to cause all containers produced by the mold source that produced the defective container to be rejected for a 20 minute interval without further testing. This is accomplished by automatically activating an ejector mechanism 19 at the container identifying apparatus station to eject all containers produced by the offending mold source as a function of the "mold sort" flag. See FIG. 1. Accordingly, the final product to be shipped will be automatically upgraded by accounting for those mold sources which have produced an objectionably high number of defective containers. A suitable ejector mechanism for this purpose is disclosed in the U.S. application Ser. No. 596,697 in connection with container identifying apparatus 18. If the "bad" flag was not set, the central processor unit resets the "divert" and "ten minute" counters as well as the 37 "bad" and "divert" flags for the particular container.

From the foregoing, it should be apparent that the "bad" flag indicates whether one of the total of four containers diverted at the increased test rate is defective. If one or more of the containers is diverted at the increased rate is defective, all containers produced in the next 20 minutes by the mold source that produced the defective diverted container will be rejected automatically to upgrade the final product to be shipped.

Exemplary Program

A computer program has been written to control a computer 44 to provide the foregoing supervisory functions. Given the above description of the operation of the closed-loop system, it is a simple task to write such a program for practicing the invention. An exemplary program is shown in flow chart form in FIGS. 11–16. A print-out of the program itself is incorporated herewith as an addendum. For the convenience of the reader, the mnemonics employed in the flow chart and print-out are identified in respect to the foregoing description of the closed-loop system in the Program Table below.

Program Table

| Mnemonic | Reference |
| --- | --- |
| SVMLD | complementary divert mold number table |
| SEQDV | divert flag |
| TESTR | results flag |
| BADSW | bad flag |
| SQCNT | divert counter |
| SQTIM | ten minute counter |
| SQMLD | divert mold number table |
| CNTTD | tracking counter |
| ACEPT | accept flag |
| CDSFT | container identifying apparatus shift flag |
| INFED | in feed flag |
| ANSTB | mold number table |
| PTSHF | pressure tested cycles table |
| PTSFT | PT shift pulse flag |
| TSTSW | in test flag |
| 40 HEX | fixed constant stored in read only memory indicates whether container in transit at scew conveyor 60 |
| ITEST | in test compare flag |
| 20 HEX | fixed constant stored in read only memory indicates good/bad status of container |

The system operation is initiated by checking the "mold sort" flag in the appropriate byte in the "test condition" table. See FIG. 11. As previously indicated, the "mold sort" flag is set if a container diverted in response to the "divert" flag proves defective. That is, the "mold sort" flag is set if a container diverted at the increased statistical testing rate proves defective.

Thereafter, all containers produced by the mold source that produced the defective diverted containers are rejected by an ejector mechanism or the like. The computer exits the loop in respect to containers produced by that mold source.

On the other hand, if the "mold sort" flag is not set, this indicates that statistical testing can proceed for the particular container identified. Thus, the "PT" flag is checked to see if the container should be diverted according to the initial statistical testing rate of one container per 20 minutes. If not, the computer exits the loop for that particular container and the container is transported by conveyor 52 to its ultimate destination without testing.

If, however, the "PT" flag is set, the central processor unit checks the "divert" flag to determine whether statistical testing should proceed at the increased rate. If the "divert" flag is set, the mold source number of the identified container is compared to the "divert mold number" table. If there is no equality, this indicates that containerss having the same mold source number are to be tested at the increased rate but should not yet be scheduled for diversion because containers from another mold source are presently being diverted and tested at the increased rate. This feature of the system is explained more fully below. The computer, therefore, exits the loop without causing the container to be diverted.

If the comparison between the mold source number of the identified container and the "divert mold number" table results in an equality, the central processor unit sends a "divert" signal to data station 46. The data station causes air pump 48 to divert the identified container to pressure tester 58 as previously described. At the same time, a "tracking" counter in the central processor unit is set to zero. This counter is advanced one count in response to each container identifying apparatus shift pulse entering the input port of the central processor unit. The counter tracks the movement of the container from the container identifying apparatus 18 through air pump 48 to acceptance by screw conveyor 60. An "accept" flag is then set to indicate that a container produced by a mold source having the identified number is in transit and scheduled for diversion to the pressure tester 58. The computer 44 then leaves the program loop and repeats the foregoing routine for the next identified container mold source number.

Synchronously, the computer 44 scans its input port to determine whether a container scheduled for diversion has actually reached switch S1 at the pressure tester 58. The routine followed by the computer is shown in FIG. 12. The input port has the data byte format shown in FIG. 8. The input byte is captured by the central processor unit and transferred to an accumulator register. See FIG. 7. The data is then transferred from the accumulator register to an internal general purpose register "C" in the central processor unit. See FIG. 12. The third bit in the byte, namely the container identifying apparatus shift pulse, is inspected and compared to its last reading (denominated "container identifying apparatus shift pulse" flag in the Program Table). If the current value of the bit does not match the last reading, the current value is stored in memory and the tracking counter is incremented one count. A mismatch indicates completion of an operating cycle by apparatus 18. This is equivalent to an increment of movement of the container. If the current value of the bit matches the last reading, the tracking counter is not incremented.

Following inspection of the container identifying apparatus shift pulse bit, the register "C" contents are restored in the accumulator register. See FIG. 12. Thereafter, bit 6 of the input byte, namely the "in feed" bit is inspected and compared to its last reading (denominated "in feed" flag in the Program Table). If the current value of the bit differs from the last reading, the current value is stored in memory and the bit is compared to a fixed constant (40 HEX) which is stored in the read-only portion of the memory. If the bit matches the fixed constant, it indicates that switch S1 at the pressure tester 58 was just tripped, that is, it indicates that the container has just been accepted at screw conveyor 60. Accordingly, the central processor unit enters the sub-routine outlined in FIG. 13.

In FIG. 13, a sub-routine is outlined for monitoring the container in transmit in screw conveyor 60. After it has been determined that the container has tripped switch S1 and has been accepted by the screw conveyor, the tracking counter contents are compared to lower and upper limits. The limits are empirically derived and specify a "time window" within which a container identified at container identifying apparatus 18 and diverted by air pump 48 should arrive at the screw conveyor. As indicated in FIG. 13, the lower limit may take on a numerical value of 50 container identifying apparatus shift pulses while the upper limit takes on a value of 90 pulses. If the tracking counter contents falls outside the "time window", the container is ignored.

If the tracking counter contents are within the "time window", the container mold source number is stored by the central processor unit in the "mold number" table. At the same time, the related entry in the "pressure tester cycles" table is set to zero. Additionally, the "twenty minute" counter portion of the corresponding byte in the "test conditions" table is set to 20 to ensure that testing of containers produced by the mold source continues at the initial rate of one container per twenty minutes.

At this point, the central processor unit input port is repeatedly scanned to signal the moment at which the container is ready for testing by the pressure tester. The contents of internal register "C" are restored to the accumulator. Bit 7 of the accumulator, namely, the pressure tester shift pulse bit, is then inspected and compared to its last reading (denominated "PT shift pulse flag" in the Program Table). If the current value of the bit does not match its last reading, the current value is stored in memory. The central processor unit then checks an "in test" flag stored in memory. The status of the "in test" flag is a function of the "in test" bit in the input port byte. The "in test" bit is generated when the container trips switch S2 at pressure tester 58. As described more fully below, the "in test" flag is set immediately prior to the container being grasped by the pressure tester jaws. If the "in test" flag has not been set, it indicates that the container is still in transit at screw conveyor 60 and that switch S2 has not been tripped by the container. The central processor unit, therefore, continues to monitor the container to determine when it is ready for pressure testing according to the sub-routine outlined in FIG. 14.

The movement of the container in transit at screw conveyor 60 is monitored by incrementing the associated entry in the "pressure tester cycles" table in response to the pressure tester shift pulses. Successively incrementing the "pressure tester cycles" table entry provides an indication of the position of each of the containers in the screw conveyor pockets.

After the "pressure tester cycles" table entry has been incremented, the internal register "C" contents are restored to the accumulator and bit 4, the "in test" bit, is inspected. See FIG. 14. The bit is compared to its last reading (denominated "test compare" flag in the Program Table). If the current value of the bit does not match the last reading, the bit is stored in the memory. If, in addition, the current value of the bit is determined to be a binary "1", indicating that switch S2 of the pressure tester has been tripped, the "in test" flag is set to binary "1". At the same time, a "results" flag located in the memory is set to binary "0".

The "results" flag is then checked for equality with a fixed constant (20 HEX) stored in the read-only portion of the memory. The fixed constant indicates that a container is defective. If there is no equality, it indicates that the container is still under test. Accordingly, the contents of internal register "C" are restored to the accumulator. Bit 5, namely the "good/bad" bit, is then inspected and the "results" flag is adjusted to reflect the test results indicated by the bit.

Figure 15:
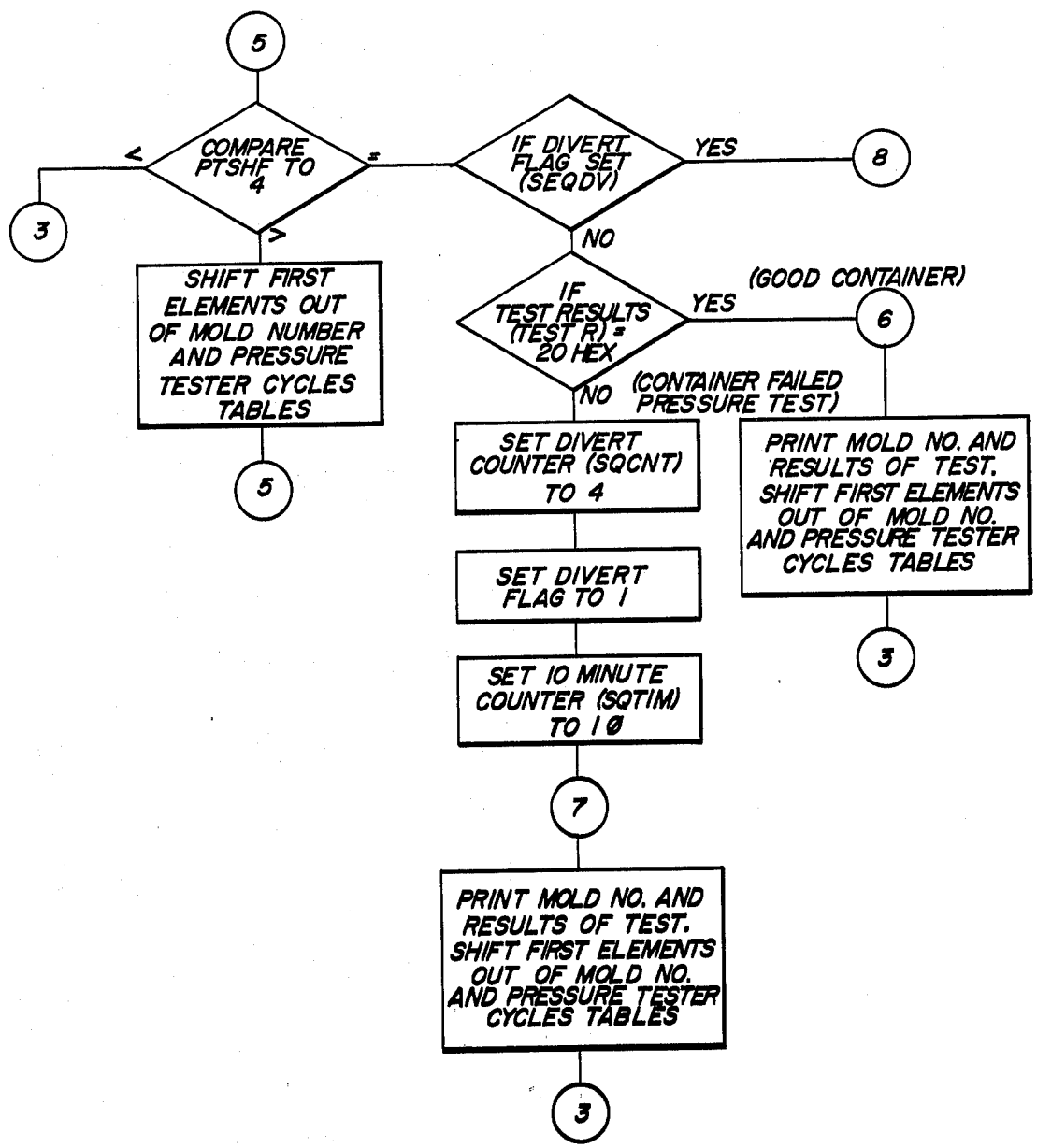
Figure 16:
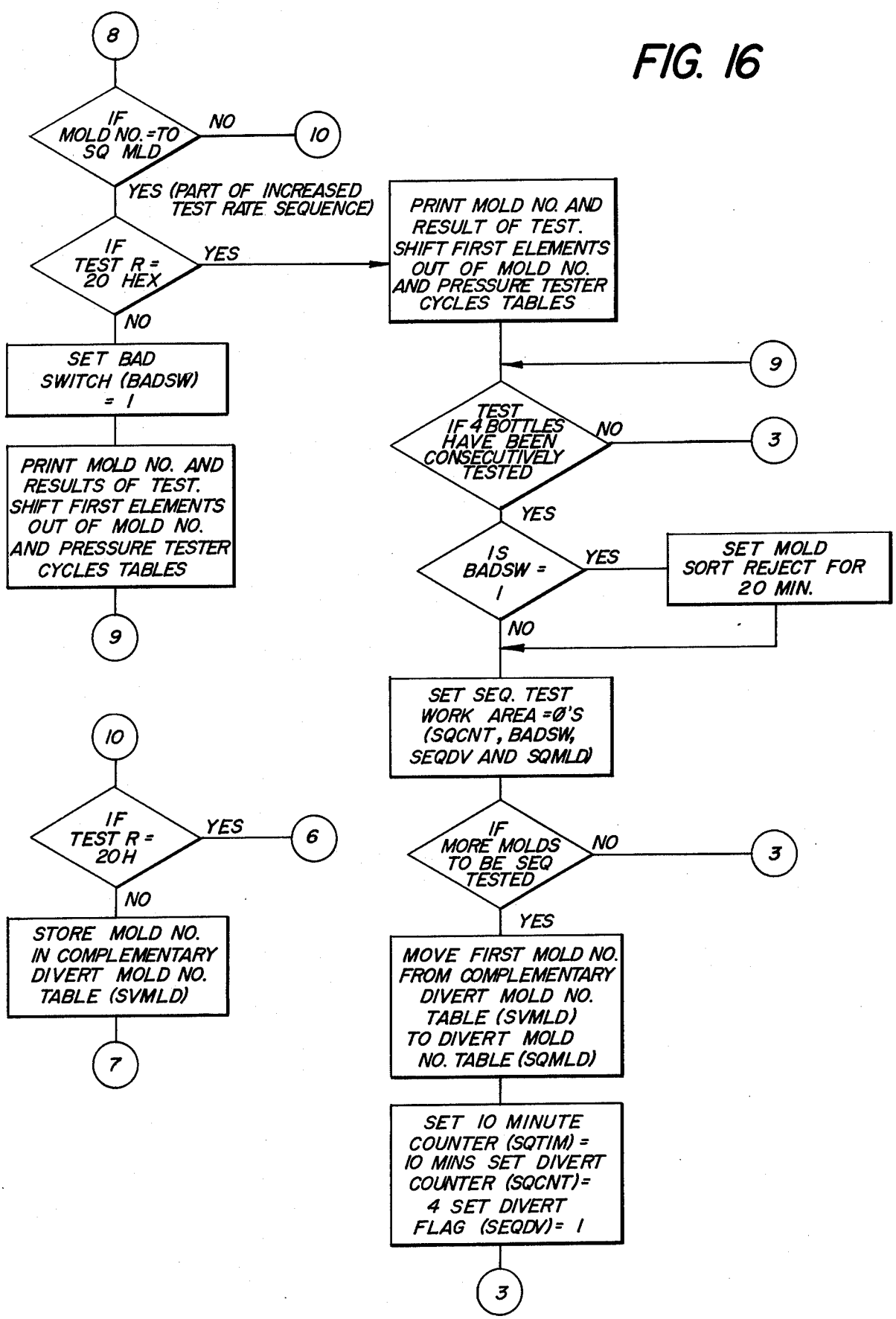

After the test results have been obtained for the container, the results are checked according to the sub-routines outlined in FIGS. 15 and 16. First, the first entry in the "pressure tester cycles" table is compared to the number 4. See FIG. 4. The significance of the number 4 in this case is that when the container trips switch S2 to indicate that it is about to be tested, the pressure tester should have completed four cycles of operation and should be entering its fifth cycle. If less than four cycles were completed at this time, it indicates that the container had been manually advanced one or more pockets along the screw conveyor. Accordingly, the test results for that container will be ignored and the central processor unit will focus on the succeeding containers. If, on the other hand, the first entry in the "pressure tester cycles" table exceeds the number 4, it indicates that the container had been manually retarded one or more pockets at the screw conveyor. In this case, the test results are again disregarded and the "mold number" and "pressure tester cycles" tables are cleared of the first entries corresponding to this container.

If the first entry in the "pressure tester cycles" table equals the number 4, it indicates that the test results can be properly applied to the container which had just been tested. Accordingly, the "divert" flag is checked to determine whether statistical testing for containers produced by the particular mold source should proceed at the increased rate. As described more fully hereinafter, the "divert" flag is set if it was determined that a container provided by the same mold source had failed the pressure test.

If no container previously produced by the same mold source had failed a pressure test, the "divert" flag would not be set. At this point, as far as the central processor unit is concerned, statistical testing will proceed at the initial rate of one container per 20 minutes. The testing rate will not be altered unless the container just tested was defective. To make this decision, the test results are checked in the next step of the sub-routine.

If the "results" flag indicates that the container is not defective, the central processor unit causes printer 118 to print the container mold source number and the test results. In addition, the first elements of the "mold number" and "pressure tester cycles" tables are shifted out. If, however, the "results" flag indicates that the container is defective, the "divert" counter is set to the number 4. The significance of the number 4 in this case is that it indicates that four containers produced by the mold source that produced the defective container shall be diverted consecutively for pressure testing at the increased rate. At the same time that the "divert" counter is set to the number 4, the "divert" flag is set to a binary "1" and a "ten minute counter" is set to 10. The "divert" flag will serve as a signal that containers identified to have been produced by the mold source which produced the defective container should be diverted consecutively for testing at the increased rate. Thereafter, the central processor unit causes printer 118 to print-out the mold source number and test results, and the first elements of the "mold number" and "pressure tester cycles" tables are shifted out.

A sub-routine for processing containers at the increased testing rate is outlined in FIG. 16. The container mold source number stored in the "mold number" table is compared to the "divert mold number" entry which is a single entry storage table. See FIG. 16. The "divert mold number" entry corresponds to a mold source which has been determined to have produced a defective container. If the mold source number of a container matches the entry, it indicates that the container is part of a sequence of four containers being consecutively pressure tested at the increased rate. If the mold source number of the container does not match the "divert mold number" entry, it indicates that the container is not part of a sequence of containers to be tested at the increased rate. The "results" flag is then checked. If the container was defective, its mold source number is stored on a "complementary divert mold number" table. This table stores entries of container mold source numbers for which testing shall proceed at the increased rate. The "complementary divert mold number" table is a FIFO table which is regularly emptied to the "divert mold number" entry.

If the mold source number of a container matches the "divert mold number" entry, the "results" flag for the container is then checked. If the "results" flag does not equal the fixed constant (20 HEX), it indicates that the container was defective. Accordingly, a "bad" flag located in the memory is set to a binary "1". Thereafter, the container mold source number and the test results are printed by printer 118 and the first entries in the "mold number" and "pressure tester cycles" tables are shifted out. The function of the "bad" switch is explained more fully in connection with the following explanation of the operation of the system when a container tested at the increased rate is determined not to be defective.

If, when the "results" flag is inspected for a container being tested at the increased rate, it is determined that the flag equals the fixed constant (20 HEX), it indicates that the container is not defective. Accordingly, printer 118 is caused to print the container mold source number and pressure tester results and the first elements of the "mold number" and "pressure tester cycles" tables are shifted out. At this point, it must be determined whether the container is the last of the four containers being tested at the increased rate. If so, the initial testing rate of one container per twenty minutes should be resumed for that mold source. For this purpose, the central processor unit checks the "divert" counter to determine whether all four containers from the particular mold source have been inspected at the increased rate. The "divert" counter contents will be zero to indicate this event.

Figure 14:
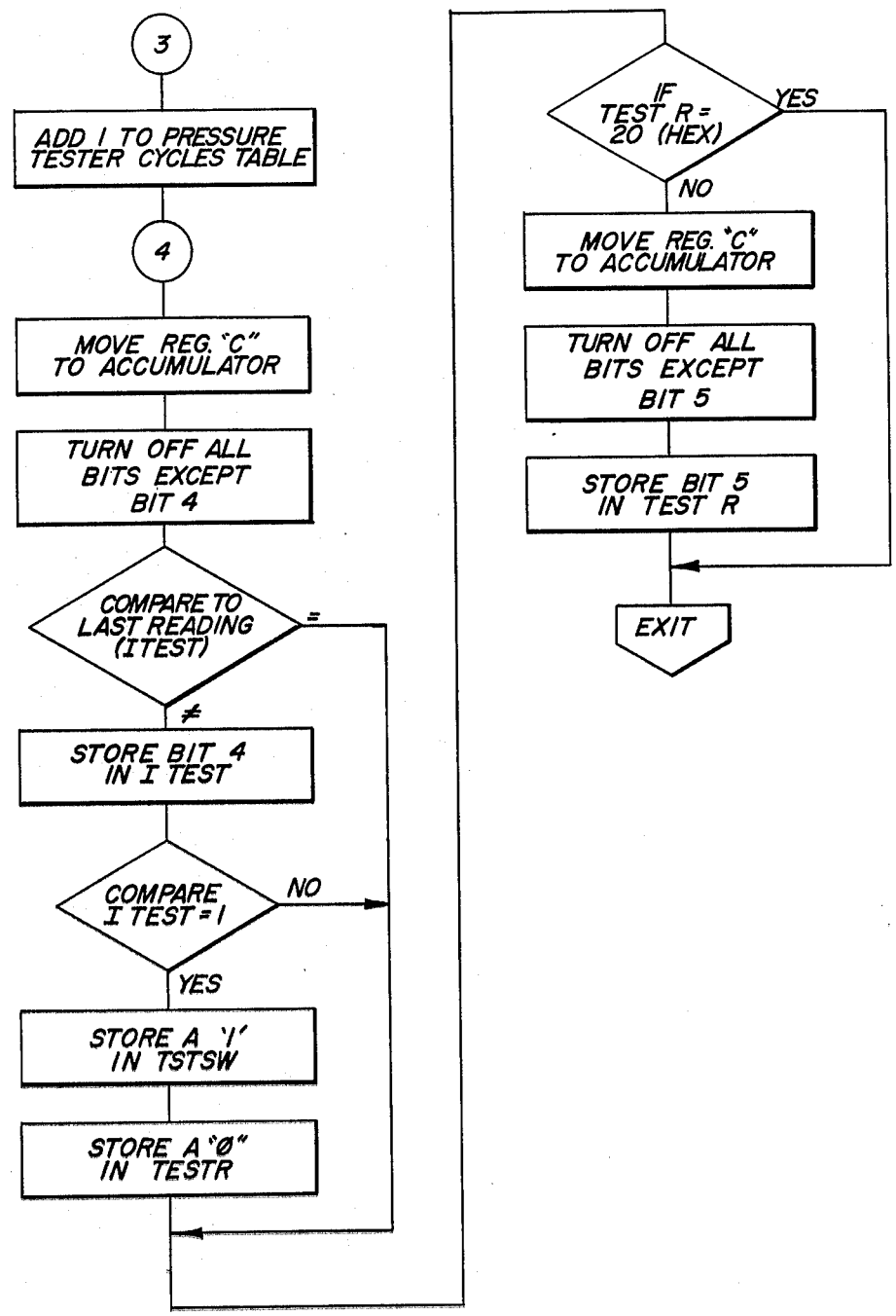

If four containers have not been tested at the increased rate, the sub-routines in FIGS. 14 and 15 are repeated for succeeding containers produced by the mold source. On the other hand, if all four containers have been tested at the increased rate, the central processor unit then checks the status of the "bad" flag. If the "bad" flag is at a binary "1", this indicates that any one or more of the four containers tested at the increased rate were defective. Accordingly, the central processor unit sets the "mold sort" flag in the appropriate byte of the "test condition" table to cause all containers produced by the offending mold source to be rejected by ejector mechanism 19 for a period of 20 minutes as determined by the "twenty minute counter" portion of the byte.

If the "bad" flag is not at a binary "1", it indicates that all four of the containers tested at the increased rate were not defective. The "divert" counter, the "bad" and "divert" flags, and the "divert mold number" entry are then cleared. The central processor unit then determines whether containers from any other mold sources are to be tested at the increased rate. This is done by inspecting the "complementary divert mold number" table. The "complementary divert mold number" table carries the mold source numbers of all containers which are to be statistically tested at the increased rate. If it is determined that the "complementary divert mold number" table is not empty, the first entry in the table is transferred to the "divert mold number" entry. The "divert mold number" entry is later inspected by the central processor unit in determining whether a container is being tested at the increased rate.

If, upon inspection of the "complementary divert mold number" table, it is determined that containers produced by other mold sources must also be tested at the increased rate, the "ten minute counter", "divert" counter and the "divert" flag are reset. Thereafter, the central processor unit monitors the containers at screw conveyor 60 in accordance with the sub-routine outlined in FIG. 14.

An advantage of the invention is that a procession of containers produced in random order by plural mold sources can be rapidly and reliably pressure tested without operator intervention. The containers can be tested at variable rates to secure the benefit of statistical quality control. Further, the final product to be shipped is automatically upgraded by discarding the product of those mold sources which have produced an objectionably high number of defective containers over fixed time periods. The invention utilizes state of the art components for identifying a container's mold source and for hydrostatically testing the container.

Although the invention has been described in connection with pressure testing of frangible containers using an advanced container identifying apparatus, it should be understood that this is only a preferred embodiment of the invention and that other equivalent embodiments may be constructed by a person of ordinary skill in the art given the instant disclosure. Thus, non-frangible and non-transparent containers may also be statistically tested according to the present invention by obvious modifications to portions of the disclosed embodiment.

In addition, the supervisory controls described herein need not be effected by a computer. The computer can be replaced by any suitable equivalent, such as a hardwired random logic circuit which performs equivalent functions in supervising the closed loop system. Of course, a hardwired random logic circuit would be relatively inflexible and expensive, but it could be used by the designer.

The program outlined in the flow charts shown in FIGS. 11–16 can be altered by the person of ordinary skill in the art to suit the requirements of a particular application. Other programs may also be substituted in place of the one described hrein to achieve the same overall system. The program outlined in the flow charts is merely presented as a representative example of a preferred technique for operating the computer. It would be a simple task, given the instant disclosure, to prepare other sets of instructions deviating from the program disclosed herein as desired.

Additionally, although the invention has been disclosed in connection with the statistical processing of a procession of containers produced by plural mold sources, it should be understood that the procession may be ordered or it may be random without affecting the spirit or scope of the invention.

Further, although a preferred embodiment of the invention has been disclosed in connection with a pressure tester 58, it should be understood that other testing units could be used as well either in conjunction with the pressure tester or in replacement thereof. For example, testing units for testing container wall thickness and dimensional gaging may also be used in the closed-loop system described herein to achieve statistical testing and upgrading of the product of plural container mold sources.

The present invention may be embodied in other specific forms without departing from the spirit or essential attributes thereof and, accordingly, reference should be made to the appended claims, rather than to the foregoing specification as indicating the scope of the invention.

ADDENDUM

EXEMPLARY PROGRAM CORRELATED TO FIGURES 11-16

Figure 11

```
2275 ;
2300 ; DIVERT ROUTINE
2325 ;
2330 LDADTSW
2335 CPI1
2340 RZ
2350 LDAMOLD
2375 MOVC,A
2400 CPI77
2425 JZNOTST
2450 MOVA,D
2475 RLC
2500 JNCNOTST; = REJECT BIT ON
2505 LDARJSW
2510 RLC
2515 JNCNOTST; JMP NO TEST - CD REJ
2525 LXIH,RJSTA
2550 MVIB,0
2575 DADB
2600 MOVA,M; GET MOLDSORT&PRESSURE TEST BYTE
2625 ANI20H; TURN OFF ALL BITS BUT 5
2650 CPI20H; SEE IF MOLD TO BE TESTED
2675 JZDTST1; TEST
2700 LDASOMLD
2725 CMPC
2750 JNZNOTST; NO TEST
2775 DTST1:
2800 LDAACEPT; GET ACCEPT SWITCH
2825 CPI0; CAN SPT ACCEPT BOTTLE
2850 JZDTST2; CAN ACCEPT BOTTLE
2875 LDACNTTD; GET CD SHIFT COUNTER
2900 CPI90
2925 JCNOTST; NO TEST
2950 DTST2:
2975 LDASEODW; GET SEQ DIVERT SWITCH
3000 CPI1; TEST IF ON
3025 JNZNOSOD
3050 LDASOCNT
3075 CPI0
3100 JZNOSOD
3125 DCRA
3150 STASOCNT
3175 LDASOMLD
3200 CMPC
```

```
3225 JNZNOTST; JMP MOLD NOS. NOT EQUAL
3250 NOSQD:
3275 MVIA,1
3300 STAACEPT; SET ACCEPT SWITCH ON
3325 LDABX; GET FULL TURN LIGHT OUTPUT
3350 ANI1; TURN BIT 1 OFF
3375 OUT1
3400 MOVA,C
3425 STADIVMD; STORE AT DIVERT MOLD NO.
3450 MVIA,0
3475 STACNTTD; ZERO CD SHIFTS TO DIVERT COUNTER
3500 NOTST:
3525 RET
3550 ;
```

Figure 12

```
20800 ;
20825 ; TEST CD SHIFT
20850 ;
20875 CKSTA:
20900 IN3
20925 MOVC,A
20950 ANI08H
20975 LXIH,CDSFT
21000 CMPM
21025 JZCKBT6; JMP NO CHG
21050 MOVM,A
21075 LDACNTTD
21080 CPI255
21085 JZARD2
21100 INRA
21125 STACNTTD
21130 ARD2:
21150 LDABX
21175 ORI2
21200 OUT1
21225 CKBT6:
21250 ;
21275 ; TEST INFEED SWITCH
21300 ;
21325 MOVA,C
21350 ANI40H
21375 LXIH,INFED
21400 CMPM
21425 JZCKBT7; JMP NO CHG
21450 MOVM,A
21475 CPI40H
21500 JNZCKBT7; INFEED SWITCH OFF
```

Figure 13

```
21525 LDACNTTD
21550 CPI15
21575 JCCKBT7; A<50 = NO GOOD
21600 CPI90; MAX COUNT
21625 JNCCKBT7; A>90 = NO GOOD
21650 LDAINDEX
21675 INRA
21700 STAINDEX
21725 MOVE,A
21750 MVID,0
21775 LXIH,ANSTB
21800 DADD
21825 LDADIVMD
21850 MOVM,A
21875 MOVB,A
21900 MVIA,0
21925 STADIVMD
21950 STAACEPT
21975 LXIH,PTSHF
22000 DADD
```

```
22025 MOVM,A
22050 LXIH,PJSTA
22075 MOVE,B
22100 DADD
22125 MOVA,M
22150 ANIOCOH; SET PT BIT OFF
22155 ORI20
22175 MOVM,A
22200 ;
22225 ; TEST PRESSURE TESTER SHIFT
22250 ;
22275 CKBT7:
22300 MOVA,C
22325 ANI80H
22350 LXIH,PTSFT
22375 CMPM
22400 JZCKBT4; NO CHG
22425 MOVM,A
22450 LDATSTSW
22475 CPI1
22500 JNZARDB7
22525 MVIA,0
22550 STATSTSW
22575 CALLTSTBL
22600 ARDB7:
```

Figure 14

```
22625 LXIH,PTSHF+1
22650 MVIB,14
22675 INXPT:
22700 MOVA,M
22725 INRA
22750 MOVM,A
22775 INXH
22800 DCRB
22825 JNZINXPT
22850 ;
22875 ; CHECK FOR BOTTLE IN TEST
22900 ;
22925 CKBT4:
22950 MOVA,C
22975 ANI10H
23000 LXIH,ITEST
23025 CMPM
23050 JNZTST1
23075 JMPCKBT5
23100 TST1:
23125 MOVM,A
23150 CPI0
23175 JZCKBT5
23200 MVIA,1
23225 STATSTSW
23250 MVIA,0
23275 STATESTR
23300 ;
23325 ; CHECK FOR BAD BOTTLE
23350 ;
23375 CKBT5:
23400 LDATESTR
23425 CPI20H
23450 RZ
23475 MOVA,C
23500 ANI20H
23525 STATESTR
23550 RET
```

Figure 15

```
23575 ;
23600 ; CHECK RESULTS OF BOTTLE TEST
23625 ;
23650 TSTBL:
```

```
23675 LXIH,PTSHF+1
23700 MOVA,M
23725 CPI4; CK NO. OF SHIFTS
23750 RC; SHIFT COUNT < 4
23775 JZSHFOK; SHIFT COUNT = 4
23800 MVIB,13
23825 LXID,ANSTB+1
23850 DOAGN:
23875 INXH
23900 MOVA,M
23925 DCXH
23950 MOVM,A
23975 INXH
24000 XCHG
24025 INXH
24050 MOVA,M
24075 DCXH
24100 MOVM,A
24125 INXH
24150 XCHG
24175 DCRB
24200 JNZDOAGN
24225 LDAINDEX
24250 DCRA
24275 STAINDEX
24300 RZ; RETURN IF INDEX = 0
24325 JMPTSTBL
24350 ;
24375 ; NUMBER OF SHIFTS OK
24400 ;
24425 SHFOK:
24450 LDASEQDV; GET SEQ DIVERT SWITCH
24475 CPI1; COMP IF ON
24500 JZSEQON; JMPIF ON
24525 LDATESTR; GET TEST RESULTS
24550 CPI20H; 20H=GOOD - 0=BAD BOTTLE
24575 JNZBOTFL; JMP BAD BOTTLE ROUTINE
24600 GDPRT:
24625 MVIA,1;SET GOOD BOTTLE PRINT SWITCH
24650 STADISSW
24675 CALLDISPT; PRINT HOLD#,AND ETC, AND SHIFT
24700 ; HOLD# OUT OF ANS TABLE
24725 RET
24750 ;
24775 ; BOTTLE FAILURE ROUTINE
24800 ;
24825 BOTFL:
24850 MVIA,4
24875 STASQCNT
24900 STASQCT1
24925 MVIA,1
24950 STASEQDV
24975 LXIH,ANSTB+1
25000 MOVA,M
25025 STASQMLD
25050 MVIA,10
25075 STASQTIM; SET TIMER FOR 10 MINS
25100 BDPRT:
25125 MVIA,2
25150 STADISSW
25175 CALL DISPT
25200 RET
```

Figure 16

```
25225 ;
25250 ; SEQ TEST ROUTINE
25275 ;
25300 SEQON:
25325 LXIH,ANSTB+1
25350 LDASQMLD
25375 CMPM
25400 JNZNTSMD; MOLD#'S NOT EQUAL
25425 LDATESTR
```

```
25450 CPI20H; 20H=GOOD - 0=BAD BOTTLE
25475 JNZSOBAD; JMP BAD BOTTLE
25500 MVIA,3
25525 STADISSW
25550 CALLDISPT; PRINT MOLD# AND ETC
25575 ENTS1:
25600 LDASOCT1
25625 DCRA
25650 STASOCT1
25675 RNZ;RET NOT ZERO
25700 DONE:
25701 LDABADSW
25702 CPI0
25703 JZBADSF
25704 LXIH,RJSTA
25705 LDASOMLD
25706 MOVE,A
25707 MVID,0
25708 DADD
25709 MOVA,M
25710 ANI80H; SET OFF ALL BITS EXECPT 7
25711 ORI20; SET REJECT AND 20 MIN COUNTER
25712 MOVM,A
25724 BADSF:
25725 MVIA,0
25750 STASOCNT
25755 STABADSW
25775 LDASVINX
25800 CPI0
25825 JNZANDCL
25850 MVIA,0
25875 STASEQDV
25900 STASOMLD
25925 RET
25950 ANDCL:
25975 LXIH,SVMLD+1
26000 MOVA,H
26025 STASOMLD
26050 INXH
26075 LXID,SVMLD+1
26100 MVIB,17
26125 SHFMD:
26150 MOVA,M
26175 STAXD
26200 INXH
26225 INXD
26250 DCRB
26275 JNZSHFMD
26300 MVIA,10
26325 STASOTIM
26350 MVIA,4
26375 STA...
26400 STASOCT
26425 LDASVINX
26450 DCRA
26475 STASVINX
26500 RET
26525 SOBAD:
26530 MVIA,1
26535 STABADSW
26550 MVIA,4
26575 STADISSW
26600 CALLDISPT; PRINT MOLD# AND ETC
26850 JMPENTS1
26875 ;
26900 ; SEQ DIVERT MOLDS NOT EQUAL
26925 ;
26950 NTSMD:
26975 LDATESTR
27000 CPI20H; 20H=GOOD - 0=BAD BOTTLE
27025 JZGDPPT; JMP GOOD BOTTLE
27050 LXIH,SVMLD
27075 LDASVINX
27100 MOVE,A
27125 MVID,0
```

```
27150 DADD
27175 LDA,ANSTB+1
27200 MOVE,A
27225 JMPBDPRT
```

Figures 15 and 16

```
27250 ;
27275 ; BUILD PRINT LINE OF PT RESULTS
27300 ;
27325 DISPT:
27350 LXIH,ANSTB+1
27375 MOVE,M
27400 MVID,0
27425 LXIH,PASS
27450 DADD
27475 DADD
27500 MOVB,M
27525 INXH
27550 MOVC,M
27575 DCXB
27600 MOVL,C
27625 DCXH
27650 MOVE,D
27675 LHLDTPAS
27700 DCXH
27725 SHLDTPAS
27750 LXIH,PTGT
27775 DADD
27800 DADD
27825 MOVB,M
27850 INXH
27875 MOVC,M
27900 INXB
27925 MOVL,C
27950 DCXH
27975 MOVE,B
27980 LHLDTPRT
27985 INXH
27990 SHLDTPRT
28000 PUSH D
28025 LXIH,CMOLD
28050 LXID,SPTLN
28075 MVIB,6
28100 PTAG1:
28125 MOVA,M
28150 STAXD
28175 INXH
28200 INXD
28225 DCRB
28250 JNZPTAG1
28275 LXIH,ANSTB+1
28300 MOVA,M
28325 STABINNO
28350 PUSHD
28375 MVIA,6
28400 LXID,BINNO
28425 LXIH,HEXBF
28450 CALLTOASC
28475 POPD
28500 MVIM,0
28525 INXH
28550 MOVA,M
28575 STAXD
28600 MVIM,0
28625 INXH
28650 INXD
28675 MOVA,M
28700 STAXD
28725 MVIM,
28750 INXD
28775 MVIA,20H
28800 STAXD
28825 INXD
```

```
28850 LDADISSW
28875 CPI1
28900 JZGDCON
28925 CPI2
28950 JZFDCON
28975 CPI3
29000 JZGDCON
29025 FDCON:
29050 POPH
29075 LXIH,FAILD
29100 JMPPTAG2
29125 GDCON:
29150 POPH
29175 PUSHD
29200 XCHG
29225 LHLDTPTG
29250 INXH
29275 SHLDTPTG
29300 LXIH,PGOD
29325 DADD
29350 DADD
29375 MOVB,M
29400 INXH
29425 MOVC,M
29450 INXB
29475 MOVM,C
29500 DCXH
29525 MOVM,B
29530 LXIH,PJSTA
29532 DADD
29534 MOVA,M
29536 ANI0C9H
29538 ORI20
29540 MOVM,A
29550 POPD
29575 LXIH,GOOD
29600 PTAG2:
29625 MVIB,6
29650 PTAG3:
29675 MOVA,M
29700 STAXD
29725 INXH
29750 INXD
29775 DCRB
29800 JNZPTAG3
29825 MVIA,20H
29850 STAXD
29875 INXD
29900 LXIH,HOUR
29925 CALLBCDAS
29950 INXH
29975 CALLBCDAS
30000 MVIA,20H
30025 STAXD
30050 INXD
30075 LXIH,DATE
30100 CALLBCDAS
30125 MVIA,2FH
30150 STAXD
30175 INXD
30200 INXH
30225 CALLBCDAS
30250 MVIA,2FH
30275 STAXD
30300 INXD
30325 INXH
30350 CALLBCDAS
30375 MVIA,2CH
30400 STAXD
30425 INXD
30450 MVIB,6
30475 LDADISSW
30500 CPI2
30525 JZNORET
30550 JCNORET
```

```
30575 LXIH,PTEST
30600 JMPPTAG4
30625 NORET:
30650 LXIH,SPACE
30675 PTAG4:
30700 MOVA,M
30725 STAXD
30750 INXH
30775 INXD
30800 DCRB
30825 JNZPTAG4
30850 LXIH,STKPL
30875 LDAPLINX
30900 CPI0
30925 JZPTAG6
30950 MVIE,37
30975 MVID,0
31000 PTAG5:
31025 DADD
31050 DCRA
31075 JNZPTAG5
31100 PTAG6:
31125 XCHG
31150 LXIH,SPTLN
31175 MVIB,37
31200 PTAG7:
31225 MOVA,M
31250 STAXD
31275 INXH
31300 INXD
31325 DCRB
31350 JNZPTAG7
31375 LDAPLINX
31400 INRA
31425 STAPLINX
31450 RET
31475 ;
31500 ; PRINT RESULT OF PRESSURE TEST
31525 ;
31550 PPTAG:
31575 LXIH,STKPL
31600 MVIB,37
31625 CALLSTPNT
31650 CALLCRLF
31675 LDAPLINX
31700 DCRA
31725 STAPLINX
31750 RZ; RETURN IF ZERO
31775 LYIH,STKPL+37
31800 LXID,STKPL
31825 MOVC,A
31850 PTAG8:
31875 MVID,37
31900 PTAG9:
31925 MOVA,M
31950 STAXD
31975 INXH
32000 INXD
32025 DCRB
32050 JNZPTAG9
32075 DCRC
32100 JNZPTAG8
32125 JMPPPTAG
32150 ;
```

We claim:

1. A method of statistically testing containers which are moved in a procession to a location at which the containers can be diverted to a pressure test station, each container having identifying indicia in respect to at least one of a plurality of mold sources, comprising:

automatically identifying each of said containers according to said identifying indicia provided on the containers before said containers are moved to said location at which they can be diverted, automatically tracking the movement of each identified container in said procession to said location.

diverting selected identified containers produced by at least one preselected mold source from said procession at said location at a first predetermined rate under computer control, automatically pressure testing the diverted containers, and providing a signal indicative of whether each tested container is defective.

2. A method according to claim 1 including the steps of storing a signal indicative of said container identification, storing said signal indicative of the result of said pressure testing step, and automatically printing a report of container identification correlated with pressure testing results as a function of said stored signals.

3. A method according to claim 1 wherein said selectively diverting step including selectively diverting other identified containers produced by said preselected mold source at a second predetermined rate effectively greater than said first predetermined rate if said signal indicates that at least one of said tested containers is defective.

4. A method asccording to claim 3 wherein said step of selectively diverting containers at said second predetermined rate includes consecutively diverting a predetermined number of said containers produced by said preselected mold source.

5. A method according to claim 1 wherein said pressure testing step includes introducing water into said container under pressure without supporting said container from below.

6. A method of automatically upgrading a procession of containers produced by plural container mold sources, comprising:

automatically identifying each container produced by said plural container mold sources, diverting selected identified containers produced by at least one preselected mold source to a pressure test station at a first predetermined rate under computer control automatically pressure testing the containers diverted at the first predetermined rate to determine whether each diverted container is defective, selectively diverting other identified containers produced by said preselected mold source at a second predetermined rate effectively greater than said first predetermined rate if at least one of said tested containers is determined to be defective, automatically pressure testing the containers diverted at the second predetermined rate to determine whether each such diverted container is defective, and automatically rejecting all other identified containers produced by said preselected mold source over a fixed period of time if at least one of said containers diverted at the second predetermined rate is determined to be defective.

7. A method according to claim 6 wherein said step of selectively diverting containers at said second predetermined rate includes consecutively diverting a predetermined number of said containers produced by said preselected mold source.

8. Apparatus for statistically testing containers which are moved in a procession to a location at which the containers can be diverted to a pressure test station, each container having identifying indicia in respect to at least one of a plurality of mold sources comprising:

means for automatically identifying each of said containers according to said identifying indicia provided thereon before said containers are moved to said location at which they can be diverted, means for automatically tracking the movement of each identified container in said procession to said location, means disposed at said location for diverting said identified containers produced by at least one predetermined mold source from selected procession at a first predetermined rate, and a pressure test station for pressure testing said diverted containers automatically and for providing a signal indicative of whether each tested container is defective.

9. Apparatus according to claim 8 including means for selectively diverting other identified containers poduced by said preselected mold source to said pressure station at a second predetermined rate effectively greater than said first predetermined rate if said signal indicates that at least one of said tested containers is defective.

10. Apparatus for automatically upgrading a procession of containers produced by plural container mold sources, comprising:

means for automatically identifying each container produced by said plural container mold sources, a pressure test station for automatically testing a container and providing a signal indicative of whether the container is defective, means for diverting selected identified containers produced by at least one preselected mold source to said pressure test station, computer means for causing said diverting means to divert selected identified containers produced by said preselected mold source to said pressure test station at a first predetermined rate until said pressure test signal indicates that at least one of said diverted containers is defective and at a second predetermined rate effectively greater than said first predetermined rate thereafter, means for rejecting all identified containers produced by said preselected mold source over a fixed period of time if said pressure test signal indicates that at least one of said containers diverted at said second rate is defective.

11. Apparatus according to claim 10 wherein said computer means for causing said diverting means to selectively divert the containers at the second predetermined rate includes means for consecutively diverting a predetermined number of containers produced by said mold source.

12. A closed loop system for statistically testing containers which are moved in a procession to a location at which the containers can be diverted from the procession, comprising:

means for automatically identifying each of said containers, means for automatically tracking the movement of each identified container in said procession to said location, means disposed at said location for diverting selected identified containers produced by at least one preselected mold source from said procession at regular intervals of time at a first predetermined rate, a pressure test station for pressure testing said diverted containers, and means for providing a signal indicative of whether each tested container is defective.

13. A closed loop system according to claim 12 including means for selectively diverting other containers produced by said preselected mold source to said pressure test station at a second predetermined rate effectively greater than said first predetermined rate if said signal indicates that at least one of said tested containers is defective.

14. A method of statistically testing containers which are moved in a procession to a location at which the containers can be diverted to a test station, each container having identifying indicia in respect to at least one of a plurality of mold sources, comprising:
   automatically identifying each of said containers according to said identifying indicia provided on the containers before said containers are moved to said location at which they can be diverted,
   automatically tracking the movement of each identified container in said procession to said location,
   diverting selected identified containers produced by at least one preselected mold source from said procession at said location at a first predetermined rate under computer control,
   automatically testing a physical property of the diverted containers, and
   providing a signal indicative of whether each tested container is defective.

15. A method according to claim 14 including selectively diverting other identified containers produced by said preselected mold source at a second predetermined rate effectively greater than said first predetermined rate if said signal indicates that at least one of said tested containers is defective.

16. A method of automatically upgrading a procession of containers produced by plural container mold sources, comprising:
   automatically identifying each container produced by said plural container mold sources,
   diverting selected identified containers produced by at least one preselected mold source to a test station at a first predetermined rate under computer control,
   automatically testing a physical property of the containers diverted at the first predetermined rate to determine whether each diverted container is defective,
   selectively diverting other identified containers produced by the preselected mold source to said test station at a second predetermined rate effectively greater than said first predetermined rate if at least one of said tested containers is determined to be defective,
   automatically testing said physical property of the containers diverted at the second predetermined rate to determine whether each container diverted at the second rate is defective, and
   automatically rejecting all other identified containers produced by said preselected mold source over a fixed period of time if at least one of said containers diverted at the second predetermined rate is determined to be defective.

17. Apparatus for statistically testing containers which are moved in a procession to a location at which the containers can be diverted from the procession, each container having identifying indicia in respect to at least one of a plurality of mold sources, comprising:
   means for automatically identifying each of said containers according to said identifying indicia provided thereon before said containers are moved to said location at which they can be diverted,
   means for automatically tracking the movement of each identified container in said procession to said location,
   means disposed at said location for diverting selected identified containers produced by at least one preselected mold source from said procession at a first predetermined rate, and
   a test station for testing a physical property of said diverted containers automatically and for providing a signal indicative of whether each tested container is defective.

18. Apparatus according to claim 17 including means for selectively diverting other containers produced by said preselected mold source to said test station at a second predetermined rate effectively greater than said predetermined rate if said signal indicates that at least one of said tested containers is defective.

19. Apparatus for automatically upgrading a procession of containers produced by plural container mold sources, comprising:
   means for automatically identifying each container produced by said plural container mold sources,
   a test station for automatically testing a physical property of a container and providing a signal indicative of whether the container is defective,
   means for diverting selected identified containers produced by at least one preselected mold source to said test station,
   computer means for causing said diverting means to divert selected identified containers produced by said preselected mold source to said test station at a first predetermined rate until said pressure test signal indicates that at least one of said diverted containers is defective and at a second predetermined rate effectively greater than said first predetermined rate thereafter, and
   means for rejecting all identified containers produced by said preselected mold source over a fixed period of time if said pressure test signal indicates that at least one of said containers diverted at said second rate is defective.

* * * * *